(12) United States Patent
Ben-Haim et al.

(10) Patent No.: US 6,236,887 B1
(45) Date of Patent: May 22, 2001

(54) DRUG-DEVICE COMBINATION FOR CONTROLLING THE CONTRACTILITY OF MUSCLES

(75) Inventors: Shlomo Ben-Haim; Nissim Darvish; Yuval Mika, all of Haifa; Maier Fenster, Petach Tikva, all of (IL)

(73) Assignee: Impulse Dynamics N.V., Curacao (NL)

( * ) Notice: Subject to any disclaimer, the term of this patent is extended or adjusted under 35 U.S.C. 154(b) by 0 days.

(21) Appl. No.: 09/254,993
(22) PCT Filed: Jul. 9, 1997
(86) PCT No.: PCT/IL97/00232
  § 371 Date: Mar. 12, 1999
  § 102(e) Date: Mar. 12, 1999
(87) PCT Pub. No.: WO98/10829
  PCT Pub. Date: Mar. 19, 1998

(30) Foreign Application Priority Data
Sep. 17, 1996 (IL) .................................................. 119261

(51) Int. Cl.[7] ......................................... A61N 1/365
(52) U.S. Cl. ............................... 607/3; 607/9; 607/68
(58) Field of Search .................... 607/9, 11, 68, 607/3, 28

(56) References Cited

U.S. PATENT DOCUMENTS

| 3,651,805 | 3/1972 | Breiling . | |
|---|---|---|---|
| 4,554,922 | 11/1985 | Prystowsky et al. . | |
| 5,083,564 | 1/1992 | Scherlag | 607/9 |
| 5,800,464 | 9/1998 | Kieval | 607/9 |
| 5,814,079 | 9/1998 | Kieval | 607/9 |
| 5,871,506 | 2/1999 | Mower . | |

FOREIGN PATENT DOCUMENTS

| 0727241 | 8/1996 | (EP) . |
|---|---|---|
| WO 97/25098 | 7/1997 | (WO) . |
| WO 98/10828 | 3/1998 | (WO) . |
| WO 98/10831 | 3/1998 | (WO) . |
| WO 98/10832 | 3/1998 | (WO) . |

OTHER PUBLICATIONS

H. Antoni., Polarization Effects of Sinusoidal 50–Cycle Alternating Current on Membrane Potential of Mammalian Cardiac Fibres, Pflugers Arch. 314, pp. 274–291 (1970).

*Primary Examiner*—Jeffrey R. Jastrzab
(74) *Attorney, Agent, or Firm*—Cowan, Liebowitz & Latman, P.C.; William H. Dippert

(57) ABSTRACT

An apparatus for the combined drug/electric-stimulation treatment of a cardiac muscle comprises circuitry (S) for creating a non-excitatory electric potential between at least two points (R1, R2) located in the vicinity of a muscle (H). A method for the combined drug/electric-stimulation treatment of a cardiac muscle, using the apparatus, involves controlling the start time, duration, and magnitude of the electric current flowing between said at least two points, to impart a desired change in cardiac muscle performance.

19 Claims, 8 Drawing Sheets

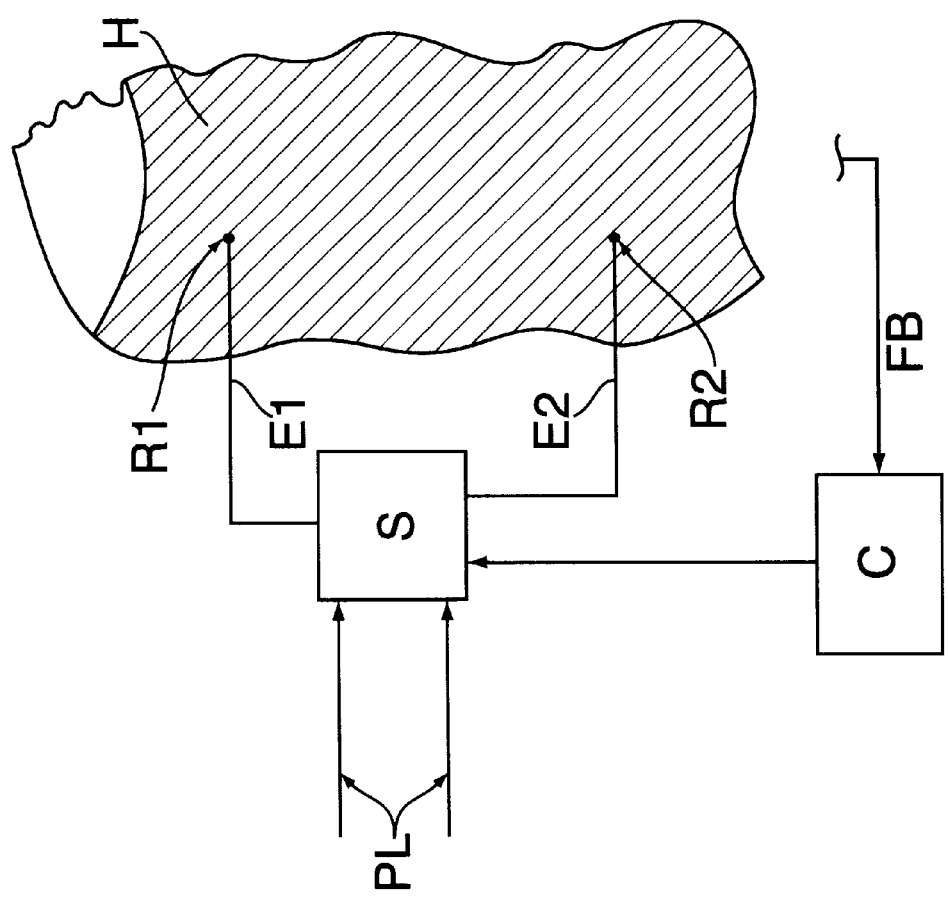

DRUG-DEVICE COMBINATION FOR CONTROLLING THE CONTRACTILITY OF MUSCLES

CROSS-REFERENCE TO RELATED APPLICATIONS

This application is a filing under 35 U.S.C. § 371 of PCT patent application No. PCT/IL97/00232, filed Jul. 9, 1997, which i based in part on commonly assigned U.S. provisional patent application Ser. No. 60/026,392, filed Sep. 16, 1996, now abandoned.

FIELD OF THE INVENTION

The present invention relates to the field of medicine. More particularly, the invention relates to means for controlling the contractility of muscles in patients treated with drugs which influence the cardiovascular system.

BACKGROUND OF THE INVENTION

Many activities of the human body involve the contraction of muscles. For instance, movement of the limbs, breathing activity, etc. The most complex and vital muscular activity of the human body is that of the heart, which functions as a pump and which, by contracting at the required times and in the required manner, controls the flow of blood throughout the body.

The heart is composed of different parts, which contract differently and with different timing, in order to permit the aforementioned pumping activity. The contraction of the heart is controlled by electric stimuli, which are generated at the cellular level by chemical reaction. However, it is well known in the art to control the timing of the contraction of the cardiac muscle, by the action of externally applied electric stimuli, through the so-called "pace maker".

In a copending PCT patent application No. PCT/IL97/00012, filed Jan. 8, 1997 by the same applicants herein, the specification of which is incorporated herein by reference, there is described a method and apparatus for modifying the force contraction of at least a portion of a heart chamber, which comprises applying a non-excitatory electric field, for a predetermined period of time, at a delay after activation, which causes the force of contraction to be increased. Substantial increases in the force of contraction are obtained, typically—but non-limitatively—in the order of 5%–50%. This increase in cardiac output is useful in order to obviate cardiac insufficiency due to a variety of pathological situations, e.g., the reduction of cardiac output due to the implantation of a pace maker, the insufficiency due to the results of the malfunctioning of a portion of the cardiac muscle, etc.

In another copending PCT/IL patent application, entitled "Apparatus and Method for Controlling the Contractility of Muscles", filed by the same applicants herein on the same day as the present application and identified as Attorney's Docket 4224/WO/97, the specification of which is incorporated herein by reference, there is described a method and apparatus for decreasing the force contraction of at least a portion of a heart chamber, which comprises applying a non-excitatory electric field of a polarity inverse of that required for obtaining an increase of muscle contractility, for a predetermined period of time, at a delay after activation, which causes the force of contraction to be decreased. The ability of reducing the contractility is of importance in a variety of situations, e.g., during surgery or as an aid in healing of hibernated areas of a heart after myocardial infarct.

Several severe diseases of the cardiac muscle cannot be treated effectively without the aid of drugs. However, many drugs used in therapy have a deleterious, side-effect in that they reduce the contractility and cardiac output of the heart and may cause life threatening arrhythmias. Some illustrative examples of drugs used in the treatment of congestive heart failure (CHE) are given below.

Congestive heart failure (CHF) is a complex clinical syndrome characterized by impaired ventricular performance, exercise intolerance, a high incidence of ventricular arrhythmias, and shortened life expectancy. Virtually all forms of heart disease can lead to heart failure, with coronary artery disease, hypertension, and diabetes mellitus being the most common in the U.S.

CHF can be broadly subdivided into two distinct forms (although several other classification schemes have been used). Distinguishing between the two forms is often difficult: 1. Diastolic dysfunction or diastolic heart failure; and 2. Systolic dysfunction or systolic CHF.

Changes in the structure and biochemical properties of the myocardium and peripheral vasculature occur during the development of CHF and these changes can contribute to further impairment of cardiovascular function. Many different drugs are used in the therapy of CHF, which affect the cardiac muscle, whether directly or indirectly, by causing changes in the cardiovascular system.

Recent studies indicate that metoprolol, a commonly used beta-blocker which can cause up-regulation of beta-1 receptors, can restore catecholamine responsiveness to patients with dilated cardiomyopathy.

Captopril, an ACE inhibitor that is commonly used to treat heart failure, has been shown to increase lymphocyte Gs and increase myocardial beta-1 receptor density.

Digitalis (cardiac glycosides): has been used clinically for over 200 years to treat heart failure and edema (dropsy), but its present use in treating CHF is controversial. Digoxin is the most widely used preparation of digitalis (half-life=1–2 days), although digitoxin (half-life=7 days) is also used in situations where long half-life may be an advantage.

However, Digoxin may be toxic at relatively low dosages, since it may cause arrhythmia and conduction problems, but the art has so far failed to provide means by which the desirable therapeutic effect of Digoxin or similar drugs may be maintained at low dosages, so as to avoid toxicity problems.

Beta-Adrenergic agonists: beta1-adrenergic agonists (dopamine, dobutamine, prenalterol, xamoterol) have been used to treat acute and chronic heart failure, but have limited usefulness in chronic CHF because of their arrhythmogenic effects, short duration of action, the development of tolerance, and necessity of parenteral administration.

Dobutamine is a moderately selective beta1-adrenergic agonist that lacks vasoconstrictor activity and causes minimal changes in heart rate. It is frequently added to nitroprusside when blood pressure is adequate to increase cardiac output.

Prenalterol and xamoterol are partial beta1-adrenergic agonists that may simultaneously stimulate beta1-receptors and block the receptors from stimulation by endogenous catecholamines, thereby protecting against beta1-receptor down-regulation.

Cyclic nucleotide phosphodiesterase (PDE-III, cGMP-inhibitable PDE) inhibitors: There are several agents that increase myocardial and vascular smooth muscle cAMP through inhibition of cyclic nucleotide phosphodiesterase PDE-III, cGI PDE) activity. These agents should therefore simultaneously increase cardiac output and reduce afterload.

The bipyridines, amrinone and mirinone, are potent PDE-III inhibitors that can be given orally or parenterally. They can be given orally, are generally well-tolerated, but can have significant non-cardiac side-effects (nausea, vomiting, thrombocytopenia).

$Ca^+$ Channel Blockers: $Ca^+$ channel antagonists are widely used in many types of heart diseases, including cardiac insufficiency, and cause direct arterial vasodilatation by the inhibition of $Ca^+$ current. Ditiazem and Verapamil exhibit negative inotropic, chronotropic and dromotropic effect on cardiac function. Some of these drugs, such as Verapamin, have life threatening side effects, such as altering the A-V node conduction.

Anti-Arrhythmic Drugs: In cardiac insufficiency, and in other ischemic diseases, many patients suffer from arrhythmia. Drugs acting on the chronicity are known to cause many side effects.

It is therefore clear that it is highly desirable to be able to reduce the dosage of such drugs, whenever possible, or to obviate side effects and problems which they may cause.

It has now been surprisingly found, and this is an object of the present invention, that it is possible to obviate the aforementioned drawbacks of drugs used in the therapy of heart diseases, by applying a non-excitatory signal of the type described above, which increases the contractility of the cardiac muscle and its output. It has further been found that this can be achieved without generating adverse effects and/or without adversely affecting the activity of the drug which is administered to the patient.

It is an object of the invention to provide apparatus for the combined drug/electric-stimulation treatment, which can be used as a treatment aid for a patient in need of a medicine which impairs heart muscle contractility.

It is another object of the invention to provide a method for treating a patient in need of a drug which may impair the contractility of the heart muscle.

It is yet another object of the invention to provide apparatus useful in therapy, by means of which the dosage of drugs having potentially harmful side effects can be reduced or, alternatively, by means of which the dosage can be increased while keeping side effects within an acceptable range.

It is still another object of the invention to provide apparatus which cooperates with such drugs, its activity being related to the amount of the drug present at a given time in the patient's blood.

Other objects and advantages of the invention will become apparent as the description proceeds.

SUMMARY OF THE INVENTION

In one aspect, the invention relates to an apparatus for the combined drug/electric-stimulation treatment of a cardiac muscle, comprising circuitry for creating a non-excitatory electric potential between at least two points located in the vicinity of a muscle.

According to a preferred embodiment of the invention, the apparatus comprises circuitry for controlling the start time of the electric potential generated between said at least two points. According to another preferred embodiment of the invention the apparatus comprises circuitry for controlling the duration of the electric potential generated between said at least two points. According to still another preferred embodiment of the invention the apparatus comprises circuitry for controlling the magnitude of the electric potential generated between said at least two points.

In a preferred embodiment of the invention the circuitry for creating a non-excitatory electric potential between said at least two points comprises one or more electrode. A variety of different electrodes can be used, which will be easily recognized by the skilled person. An illustrative example of suitable electrodes are carbon electrodes.

In another aspect, the invention is directed to apparatus for the combined drug/electric stimulation treatment, comprising circuitry for causing a non-excitatory electric current to flow between at least two points located in the vicinity of a muscle.

According to a preferred embodiment of the invention, the apparatus comprises circuitry for controlling the start time of the electric current flowing between said at least two points.

According to another preferred embodiment of the invention, the apparatus comprises circuitry for controlling the duration of the electric current flowing between said at least two points.

According to still another preferred embodiment of the invention, the apparatus comprises circuitry for controlling the magnitude of the electric current flowing between said at least two points.

In a preferred-embodiment of the invention the circuitry for causing a non-excitatory electric current to flow between said at least two points comprises one or more electrode, e.g., carbon electrodes.

In another aspect the invention is directed to means and methods for counteracting proarrhythmic effects of drugs.

In the context of the present invention, by "non-excitatory current", or "non-excitatory potential", or "non-excitatory signal", it is meant to indicate a signal which does not cause a propagating action potential in the muscle cells (which may start a new pacing or contraction of the muscle). In other words, the non-excitatory electric stimulation effected by a non-excitatory electric pulse is such that it does not induce propagating activation potentials in the cardiac muscle cells. Rather, such pulses affect the response of the heart muscle to the action potentials, by modulating cell contractility within selected segments of the cardiac muscle. As described in the abovementioned PCT patent application PCT/IL97/00012, the inventors have found that by applying non-excitatory electrical stimulation pulses of suitable strength, appropriately timed with respect to the heart's electrical activation, the contraction of the selected segments can be increased or decreased, thus increasing or decreasing the stroke volume of the heart.

There may be various reasons for a signal to be non-excitatory. Two main types of non-excitatory signals to be used in conjunction with the invention are: 1) A signal which, independently of its magnitude, is applied during the refractory period, and therefore does not cause a new contraction, even though its magnitude may be above threshold values for pacing; 2) A signal which is sub-threshold for pacing and, therefore, no matter when given, does not cause a new contraction to take place.

While a DC current is typically used as the base line for the non-excitatory signal, it is possible to supply a signal which is a complex signal for instance, a signal generated by superimposing an AC current on the DC base signal so as to generate a waveform of varying envelope. Any suitable signal can be superimposed, having any shape, e.g., square wave or sinusoidal wave, as will be apparent to the skilled person. Thus, according to one preferred embodiment of the invention the apparatus further comprises means for superimposing on a DC signal one or more waveforms of given frequency and amplitude, thereby to generate a complex signal.

The apparatus of the invention can be provided in different forms, e.g., as an insertable device or an extra corporal device or an implantable device.

According to a preferred embodiment of the invention, the circuitry for controlling the start time and/or duration of the electric potential is synchronized to heart activity, for instance, it can operate not at every beat of the heart, e.g., every 1, 2 or 3 beats of the heart.

According to a preferred embodiment of the invention the non-excitatory electric current is a DC electric current, and the apparatus may further comprise circuitry for superimposing on the DC signal one or more waveforms of given frequency and amplitude, thereby to generate a complex signal.

The apparatus employed to carry out the method of the invention can be of different construction, as will be apparent to the skilled person., One example of apparatus suitable for carrying out the invention is described in detail and claimed in a copending PCT patent application of the same applicants herein, entitled "Cardiac Output Controller", filed on the same day as the present application and identified as Attorney's Docket 27068, the description of which is incorporated herein by reference. Another example of suitable apparatus, coupled to a pacemaker device, is the subject of another copending PCT patent application of the same applicants herein, entitled "Cardiac Output Enhanced Pacemaker", filed on the same day as the present application and identified as Attorney's Docket 27181, the specification of which is also incorporated herein by reference. However, as said, the invention is not intended to be limited to any particular construction of device used to carry it out.

In another aspect, the invention is directed to apparatus for the combined drug/electric-stimulation treatment of a cardiac muscle, comprising:

means for creating an electric potential between at least two points located in the vicinity of the cardiac muscle;

means for causing a non-excitatory electric current to flow between said at least two point; and means for controlling the start time, duration and magnitude of the electric current flowing between said at least two points.

According to a preferred embodiment of the invention the apparatus comprises:

means for creating an electric potential between at least a pair of electrodes in the vicinity of the cardiac muscle at at least two root locations;

means for causing a non-excitatory electric current to flow between said at least two root locations; and means for controlling the start time, duration and magnitude of the electric current flowing between said at least two root locations.

By "root location" it is meant to indicate the vicinity of the muscle where the electrodes are located, which may be distinct from the area which is affected by the current flowing between them. As will be appreciated by the skilled person, due to the very complex nature of the electric behavior of the cardiac muscle, it is possible that positioning an electrode at a given location will affect another, more remote portion of the muscle. Therefore, the root location is not necessarily the center or any other portion of the treated area, but it is only a location, near the muscle, where an electrode will be positioned.

The invention is further directed to a method for the combined drug/electric stimulation treatment of a cardiac muscle, comprising a) administering to a patient in need thereof a drug which affects the cardiovascular system and which affects the cardiac muscle, or a mixture of two or more such drugs, b) creating a non-excitatory electric potential between at least two points located in the vicinity of the muscle, and c) controlling one or more of the parameters consisting of start time, duration, magnitude and polarity of the non-excitatory electric potential created between said at least two points.

In another aspect the invention is directed to a method for the combined drug/electric stimulation treatment of a cardiac muscle, comprising a) administering to a patient in need thereof a drug which affects the cardiovascular system and which affects the cardiac muscle, or a mixture of two or more such drugs, b) causing a non-excitatory electric current to flow between at least two points located in the vicinity of the muscle, and c) controlling one or more of the parameters consisting of start time, duration, magnitude and polarity of the non-excitatory electric current flowing between said at least two points.

The signal supplied to the patient according to the method of the invention is of the same type as described above with reference to the apparatus.

The change in cardiac muscle contractility and of electrophysiological characteristics of the cardiac muscle obtained by the method of the invention can be exploited for a variety of therapeutic purposes. According to one preferred embodiment of the invention, it is designed at least partially to compensate for cardiac muscle contractility decrease induced by said drug or mixture of drugs. According to another preferred embodiment of the invention it is designed at least partially to compensate for cardiac muscle contractility increase induced by said drug or mixture of drugs. According to still another preferred embodiment of the invention the change in cardiac muscle contractility is designed to add to and/or amplify the cardiac muscle contractility increase or decrease induced by said drug or mixture of drugs.

In another aspect the invention is directed to a method for reducing the dosage of a cardiovascular drug which affects cardiac muscle contractility. Thus, drugs such as Digoxin, and other proarrhythmic drugs, which as explained above have serious side effects, can be administered in substantially lower dosages, while at the same time achieving the same or even an improved effect on cardiac muscle contractility.

Thus, according to a preferred embodiment of the invention there is provided a method for the combined drug/electric-stimulation treatment of a cardiac muscle, comprising:

administering to a patient in need thereof a drug which affects the cardiovascular system and which affects the cardiac muscle, or a mixture of two or more such drugs;

providing an electric potential between at least a pair of electrodes in the vicinity of the cardiac muscle at at least two root locations;

causing a non-excitatory electric current to flow between said at least two contacting locations; and controlling the start time, duration and magnitude of the electric current flowing between said at least two root locations, so as to impart the desired change in cardiac muscle contractility.

The invention further encompasses a kit for the treatment of cardiovascular diseases, comprising a drug or a combination of two or more drugs, and an apparatus according to the invention, as herein described.

Additional apparatus according to the invention comprises circuitry for controlling its activity as a function of calculated and/or actual level of a given drug or combination of drugs in the patient's blood.

The apparatus of the invention is further useful for reducing the dosage of pro-arrhythmic drugs, and, for counteracting side-effects of pro-arrhythmic drugs.

Further therepeutic flexibility can be provided by another preferred embodiment of the invention, in which the apparatus comprises timing circuitry for activating it at predetermined times during the day.

As will be appreciated by the skilled person, the actual set of operating parameters used (current, length of pulse, number of electrodes, lag after pacing signal, etc.), will be dependent on the specific use made of the invention, and the skilled person will be able to devise the optimal set of parameters for a given application. Some non-limitative operating ranges in which cardiac muscle reacts according to the invention are given here for the sake of illustration only, it being understood that operation outside such ranges is of course possible under various conditions: Current: 0.01–10 mA; Length of Pulse: 1–998 milliseconds with a pacing of 1 Hz, and 1–498 milliseconds with a pacing of 2 Hz; Delay after Pacing Signal: 1 milliseconds and above. Where no pace maker is used, the delay is preferably calculated from the natural pacing of the patient's heart, or from the local activation time.

While a variety of electrodes can be used, and the invention is in no way limited to any particular type of electrode, particularly preferred suitable electrodes for this purpose are, e.g., carbon electrodes.

BRIEF DESCRIPTION OF THE DRAWINGS

The above and other characteristics and advantages of the invention will be more readily apparent through the following detailed description of preferred embodiments thereof with reference to the appended drawings, wherein:

FIG. 8 is a schematic representation of an apparatus according to one embodiment of the invention.

DEFINITIONS

Figure 1:
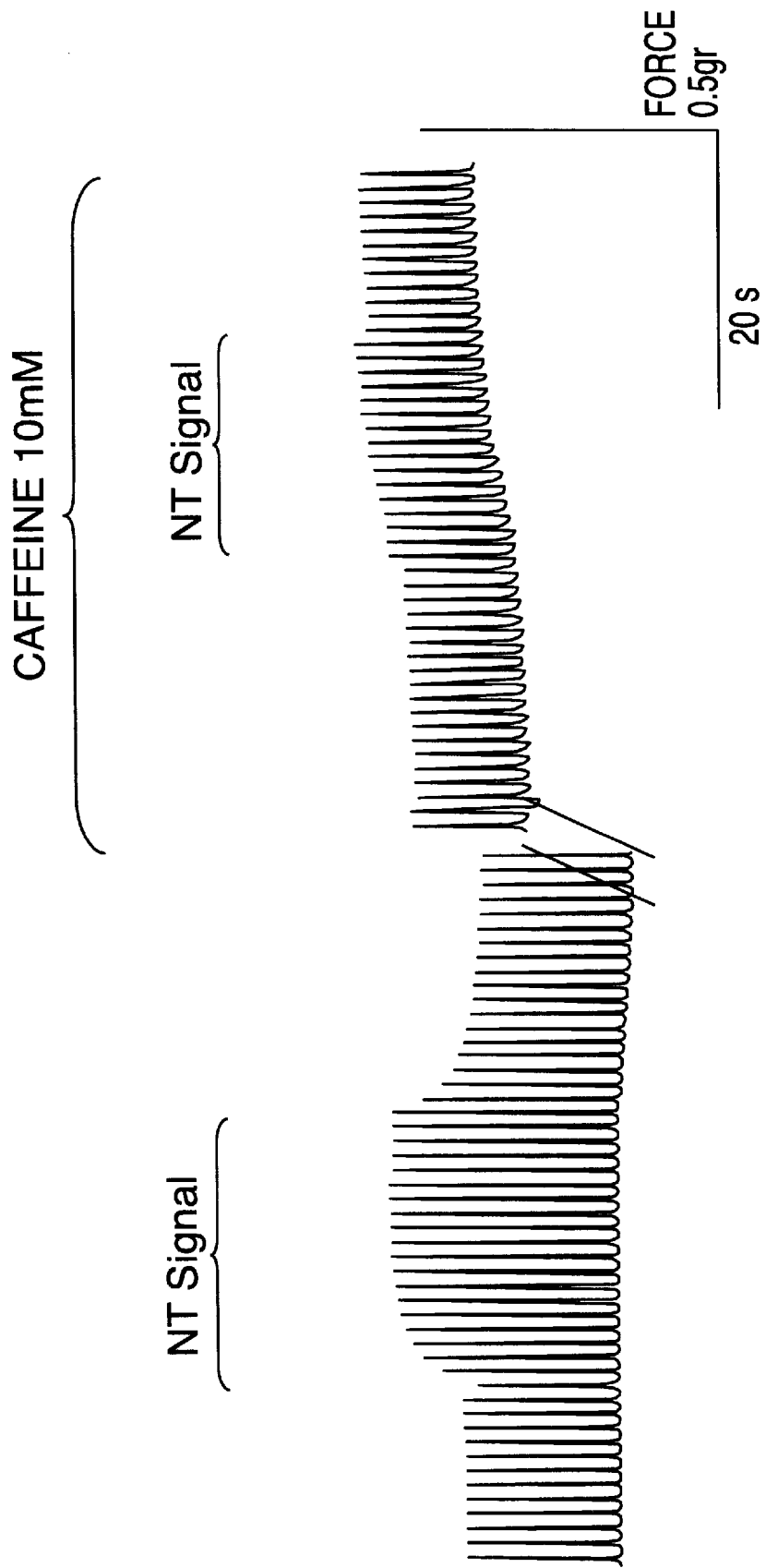
FIG. 1 shows the effect of the application of an NT-signal to a rabbit papillary muscle in the presence of Caffeine.

The following terms and abbreviations, used throughout this specification, are defined below, for the sake of clarity:
b.p.m.=Beats per minute
HMC=Hypertrophic Cardiomyopathy
I.M.=Intramuscular
IV=Intra Venous
LV=Left Ventricle
LVP=left ventricular pressure
NT Signal=Non-Excitatory Signal
RV=Right Ventricle
VF=Ventricular Fibrillation

DETAILED DESCRIPTION OF PREFERRED EMBODIMENTS

The invention will now be illustrated through detailed experiments. Experiments in vitro were carried out using isolated rabbit papillary muscle, and the protocol for its isolation is detailed below.

EQUIPMENT

The following equipment which will be referred to hereinafter, is now briefly described for the sake of clarity Plugsys system: The plugsys system is an incorporating plug in modules for measuring, controlling and data processing in connection with recorders and computers. In general, it functions as an amplifier which increases the sensitivity of the measuring of biological signals. One such device, used in the experiments described herein, is manufactured by HSE, Germany.

Millar: This device (manufactured by Millar Instruments, U.S.A.), is a micro manometers transducer that can be connected to a battery operated bridge (which is the interface box) and the output can be digitized using an A/D converter. In another mode of operation the transducer is connected through a DBA (plugsys DC Bridge Amplifier), which is an amplifier connected to transducers to measure pressure force (manufactured by HSE, Germany).

ISOLATED PAPILLARY MUSCLE PROTOCOL

Animals: New Zealand white rabbits (males) from Israel (Yokneam) or an hybrid of New Zealand White and local albino rabbits (males, AniLab, Rehovot) are kept in room temperature, 2–3 per cage (35×55×65 cm), under natural light conditions. Daily feeding of dry food (Rabbit Mix-Code 590), and unlimited water supply. The cages and the room are cleaned daily, Instruments:

A. for solution making: Scales (by Mettler toledo, model P8303, Max 310 gram, d=1 mGram) magnetic stirrer. by Freed electric. Weights 10 Kg (d=50 gram) by Moznei Shekel, Gas tanks with mixed 95% $O_2$+5% $CO_2$" pressure regulators, pH meter by Mettler toledo, model 320 PH, ice machine 45 Labotal.

B. for the in-vitro papillary muscle preparation

Dissection chamber (HSH, Hugo Sachs Elektronik, Germany), Steered organ bath type 813 (I-18E) including temperature controller type 319, Force Transducer type F30 with amplifier type 660 and calibration unit (HSE), Stereoscope (Olympus), Digital micro manipulator (HSB), Manipulator, Anti-vibration table (IMC, U.S.A.), Faraday cage, Fiber optic illuminator (HSE), Current and Voltage clamp amplifier (axon Instruments, U.S.A.), stimulators (Grass instruments, U.S.A.), Micro-pipette puller by Narishige (model pp-83, Japan) Current source ISO 10 and ISO-50 (home made) supplying 10 and 50 mA correspondingly and Oscilloscope, 20 MHz (Gould, England), Computers: PowerPC 9500/I50, (Apple, U.S.A.), or Pentium, 160 MHz, Data Acquisition Boards: PC-AO-2DC, 16 bite, or the PCI-M10 8, 12 bite board by National Instrument, software: LabView for windows, by National Instrument (U.S.A.). Data acquisition and analysis program are home made, The program includes data acquisition and on-line analysis, programmable experiment execution, programmable signal output. The off-line analysis program analyze different parameters of muscle twitch and action potentials.

Solution:

The Krebs-Heseleit Solution (KHS) was prepared using materials from Sigma (Israel): 0.32 g/lit KCl (4.5 mM), 6.99 g/lit NaCl (118.0 mm, 2.01 g/lit NaHCO$_3$ (24.0 mM), 0.285 g/lit MgSO$_4$·7H$_2$O (1.19 mM, 0.16 g/lit KH$_2$PO$_4$ (1.18 mM), 2.0 g/lit Glucose (11.0 mM), and 0.37 g/lit CaCl$_2$·2H$_2$O (2.52 mM), added after bubbling with a 95% O$_2$+5% CO$_2$ gas mixture for 20 minutes.

Solution preparation: Distilled water (ion exchange column Zilion, Israel and ultra filtration by EasypurLF, Israel) are used to prepare the KHS stock solution (X 20, 5 L). The chemicals listed above except CaCl$_2$ are used. The stock solution expire after 1 week of refrigeration, For each day of experiment fresh solution is prepared (5 L) out of the stock solution, CaCl$_2$ is added, and the solution is bubbled (95% O$_2$/15% CO$_2$) for 20 min. and titrated to a pH of 7.4. Bubbled KHS at room temperature is used for perfusion of the papillary muscle kept in the Steiert organ chamber. Ice cold (4 C), bubbled EKS is used for the dissection of the papillary muscles.

Anesthesia and heart dissection: animal is brought from the cage to a scale for measuring body weight, The animal is anesthetized by 1Vembutal 1–1.2 mg 1 Kg body weight I.P, using –5 cc syringe and 23 Gage needle. The level of anesthesia is checked by the animal reflex to a pinch. When the animal is deeply anesthetized, the skin over the chest is cut off and the chest wall is cut exposing the heart. Using seizures and a forceps the pericardium is cut and the heart is dissected out by cutting all the blood vessels, Immediately after cutting, the heart is placed in an ice cold and oxygenated KHS.

Papillary muscle dissection: The heart is transferred to a fresh ice-cold KHS and than to the dissection chamber, containing ice-cold continuously oxygenated KHS. The heart is fixed to a rubber pad with insect pins and than the left ventricle is opened exposing the papillary muscles. A silk (60) thread is tight around the tendon of the papillary muscle and the muscle is dissected out using fine twizers. The dissected muscle (length of 2–3 mm) is transferred to the organ bath and the heart is kept in the dissection chamber at 4° C. for further dissections of the other papillary muscles. The dissection of the papillary muscle last for 3–5 min.

The Steiert Organ Bath: The muscle is placed in an organ bath, and than fixed to the chamber by a plastic holder. The silk thread tight to the tendon is hooked to a rigid hook on the force transducer (on the opposite side) to give an isometric conditions. The papillary muscle is continuously perfused (7–12 ml/min,) with oxygenated KHS kept at a regulated temperature of 37° C.

Pacing and Stimulation:

Pacing stimuli (typically 1 Hz, 2 ms duration, and amplitude of 2 mA) are given by two Ag-AgCl electrodes which are part of the organ bath and are placed under the muscle. The electrodes are covered with AgCl layer, chloridizing by 5 mA, 5 ms pulses during perfusion. Constant current stimuli (CCLU) are given to the upper part of the muscle using graphite electrodes (diameter of 0.5 mm fitted to a glass pipette) placed 2–3 mm apart along the fibers' line (contraction axis). The muscle length is adjusted to maximal isometric force and left for equilibration period of 30 min.

Drug administration:

We use the perfusion system for drug application by switching the feeding krebs solution bottle to the drug containing bottle. The drug is administered for a period of 30–80 minutes while monitoring the mechanical and electrophysiological response of the muscle every 10 minutes.

EXAMPLE 1

Stimulation in the presence of Caffeine

A rabbit papillary muscle was stimulated by an NT-signal in the presence of Caffeine 10 mM (Phosfodiesterase Inhibitor).

A rabbit papillary muscle was stimulated in Organ-Bath perfused by KHS (normal experimental medium) together with Caffeine 10 mM (which is a PDE inhibitor and also causes depletion of the internal cardiac Ca$^+$ stores—Sigma, Mo, catalog No. C-8960) for 60 in before applying the NT signal The NT-signal applied to the electrodes 4 produced an average increase in peak force of the control. Caffeine 10 mM when applied cause a significant reduction in the basal contraction force (33% decrease). It also reduced the increase in peak force in response to NT stimulation applied to the same preparat in the presence of Caffeine to an average increase of 15% in the muscle force, vs 60% increase in the control level.

Parameters:

Pacing: 1 Hz, 2 mS Duration, 1 mA current.

NT signal: 30 mS Delay, 60 mS Duration, 6 mA, with the polarity increasing muscle contractility.

Temp. 36.2° C.

The results are shown in FIG. 1.

EXAMPLE 2

Stimulation in the Presence of Ryanodine

A rabbit papillary muscle was stimulated in Organ-Bath perfused by KHS together with Ryanodine (a Ca-release suppresser from the Sarcoplasmic Reticulume). 100 nM (Sigma, Mo, catalog No. R-6017) for 60 min before applying the NT signal.

The NT-signal applied to this preparat produced an average increase in peak force of 60% in the control. Ryanodine 100 nM when applied cause a significant reduction in the basal contraction force (55% decrease). However when NT stimulation was applied to the same preparat in the presence of Ryanodine, it produced an average increase of 70% in the muscle force, compared to the new basal force.

Parameters:

Pacing: 1 Hz, 2 mS Duration, 1 mA current.

NT Signal: 30 mS Delay, 60 mS Duration, 6 mA.

Temp. 36.2° C.

Figure 2:
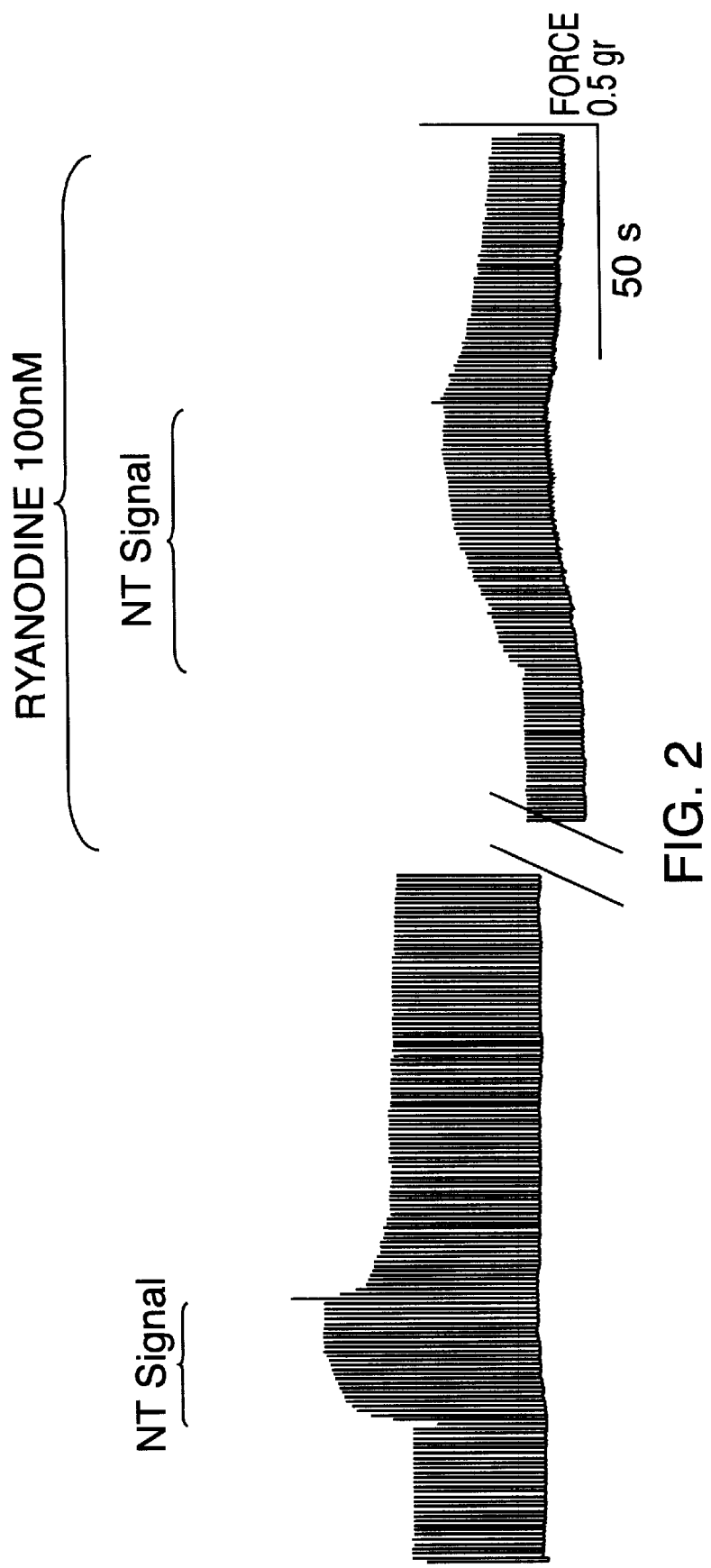
FIG. 2 shows the effect of the application of an NT-signal to a rabbit papillary muscle in the presence of Ryanodine.

The results are shown in FIG. 2.

EXAMPLE 3

Stimulation in the Presence of Nifedipine

A rabbit papillary muscle was stimulated in Organ-Bath perfused by KHS together with Nifedipine (Ca-channel blocker commonly used in clinical treatment in ischemic heart disease mainly affecting the smooth muscle cells in vascular vessels). 1 $\mu$M (Sigma. Mo, catalog No. n-7634) for 10 minutes before applying the NT Signal.

The NT signal applied to this preparat produced an average increase in peak force of 30% in the control Nifedipine 1 $\mu$M when applied cause a significant reduction in the basal contraction force (70% decrease). However when NT stimulation was applied to the same preparat in the presence of Nifedipine an average of 35% increase in the muscle force was observed.

Figure 3:
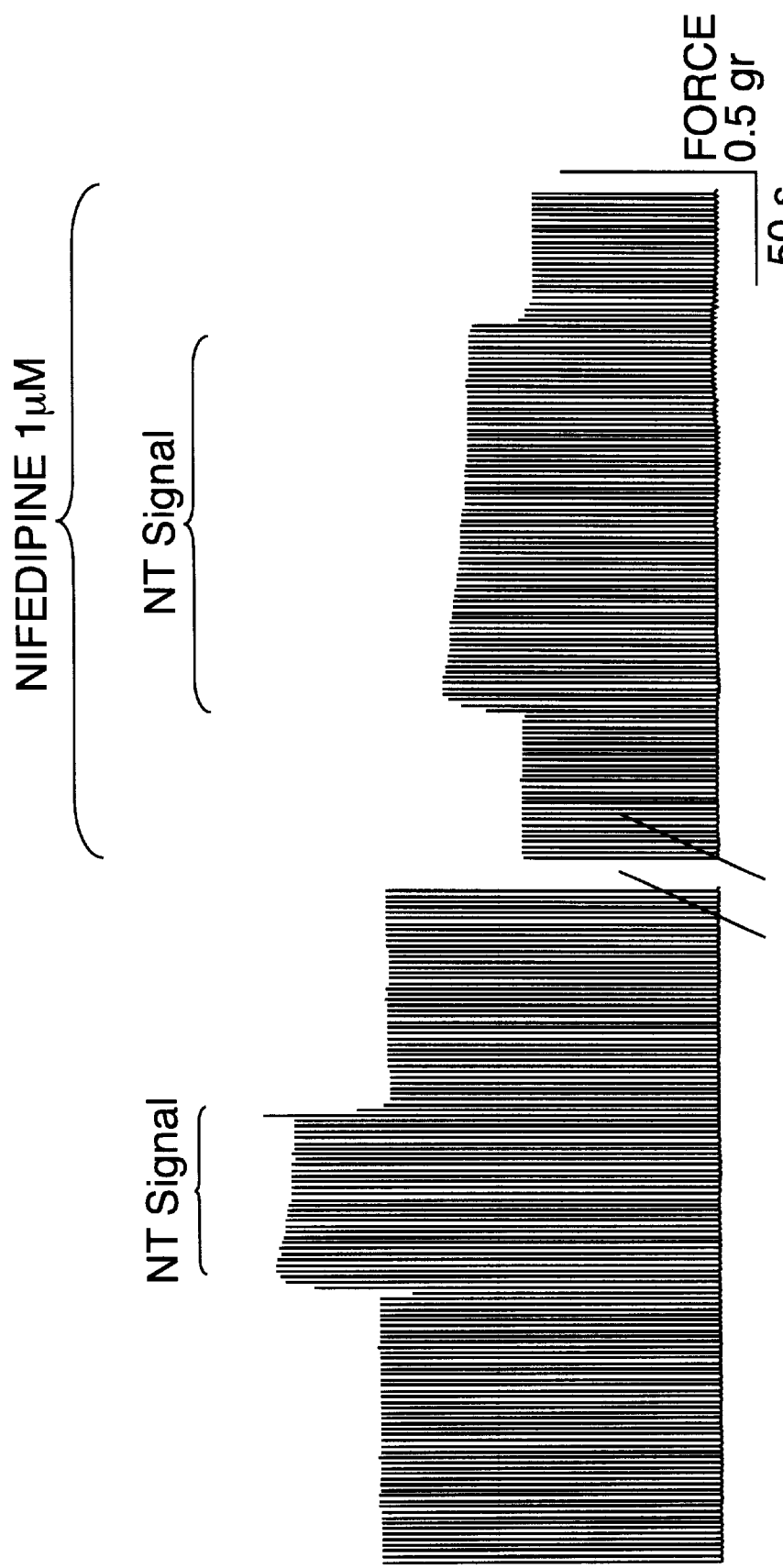
FIG. 3 shows the effect of the application of an NT-signal to a rabbit papillary muscle in the presence of Nifedipine.

Parameters:
 Pacing: 1 Hz, 2 mS Duration, 1 mA current.
 NT Signal: 30 mS Delay, 60 mS Duration, 6 mA.
 Temp. 36.2° C.
 The results are shown in FIG. 3.

EXAMPLE 4

Stimulation in the Presence of Propranolol and Adrenaline

Figure 4:
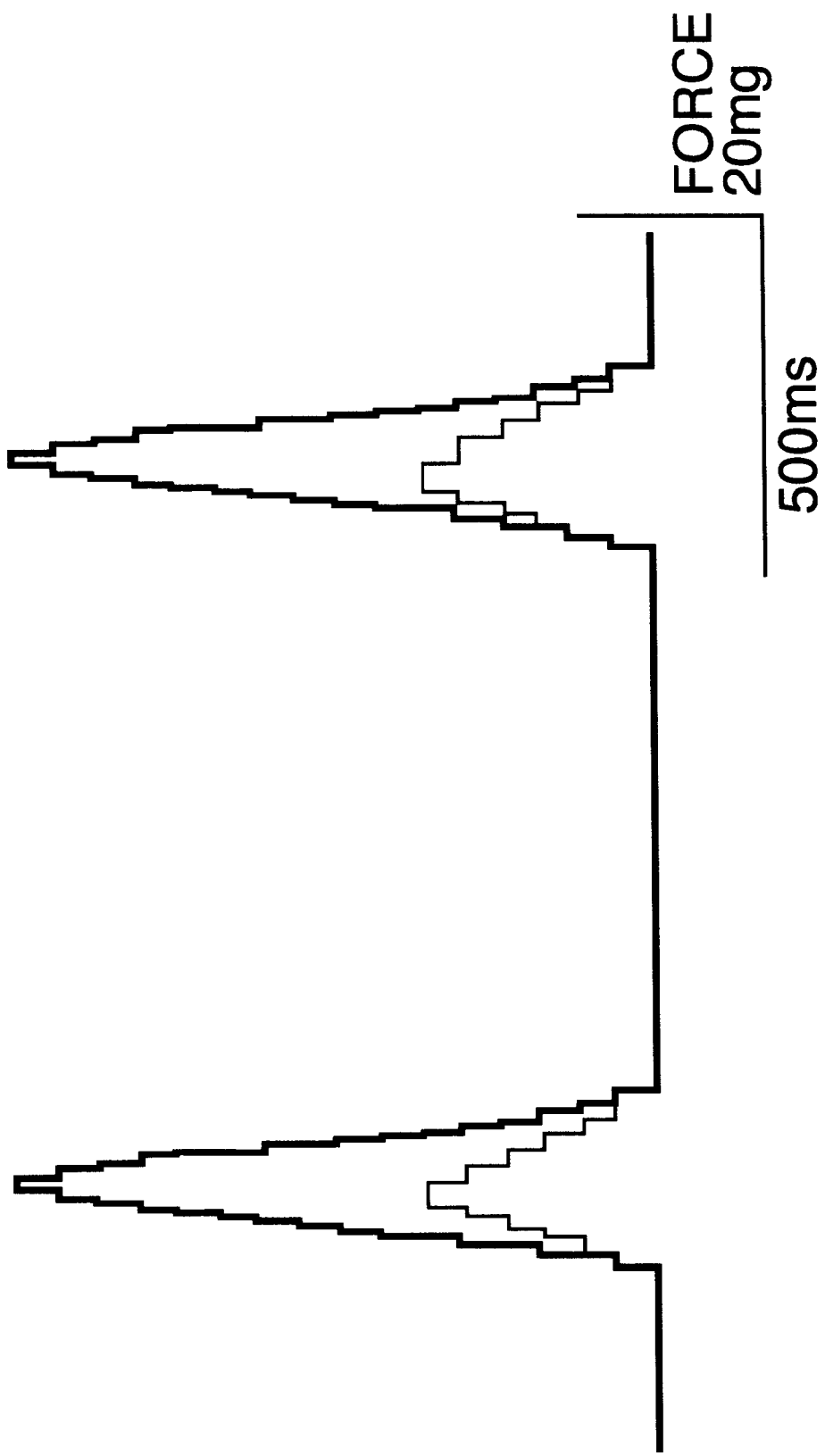
FIG. 4 shows the effect of the application of an NT-signal to a rabbit papillary muscle in the presence of both propranolol and adrenaline.

An experiment combining two drugs was carried out, the results of which are shown in FIG. 4. A rabbit papillary muscle was exposed for 5 minutes to propranolol (0.5 µM) and adrenaline (0.25 µM) in control Now amplitude trace) and activated by the NT signal (high amplitude trace).

The graph depicts twitches of papillary muscle after 5 min exposure to the above. The concomitant presence of the drugs decreased the overall muscle force. When the NT signal was applied, the contractile force increased by about 200%. The control trace reflects the clinical state of heart failure, with reduced contractility, high plasma catecholamine concentration, while there is down regulation of the Beta receptors.

Parameters:
 pacing: 1 Hz, 2 mS duration, 3 mA.
 NT Signal: 30 mS delay, 60 mS duration, 6 mA.

EXAMPLE 5

Stimulation in the Presence of Adrenaline

Figure 5:
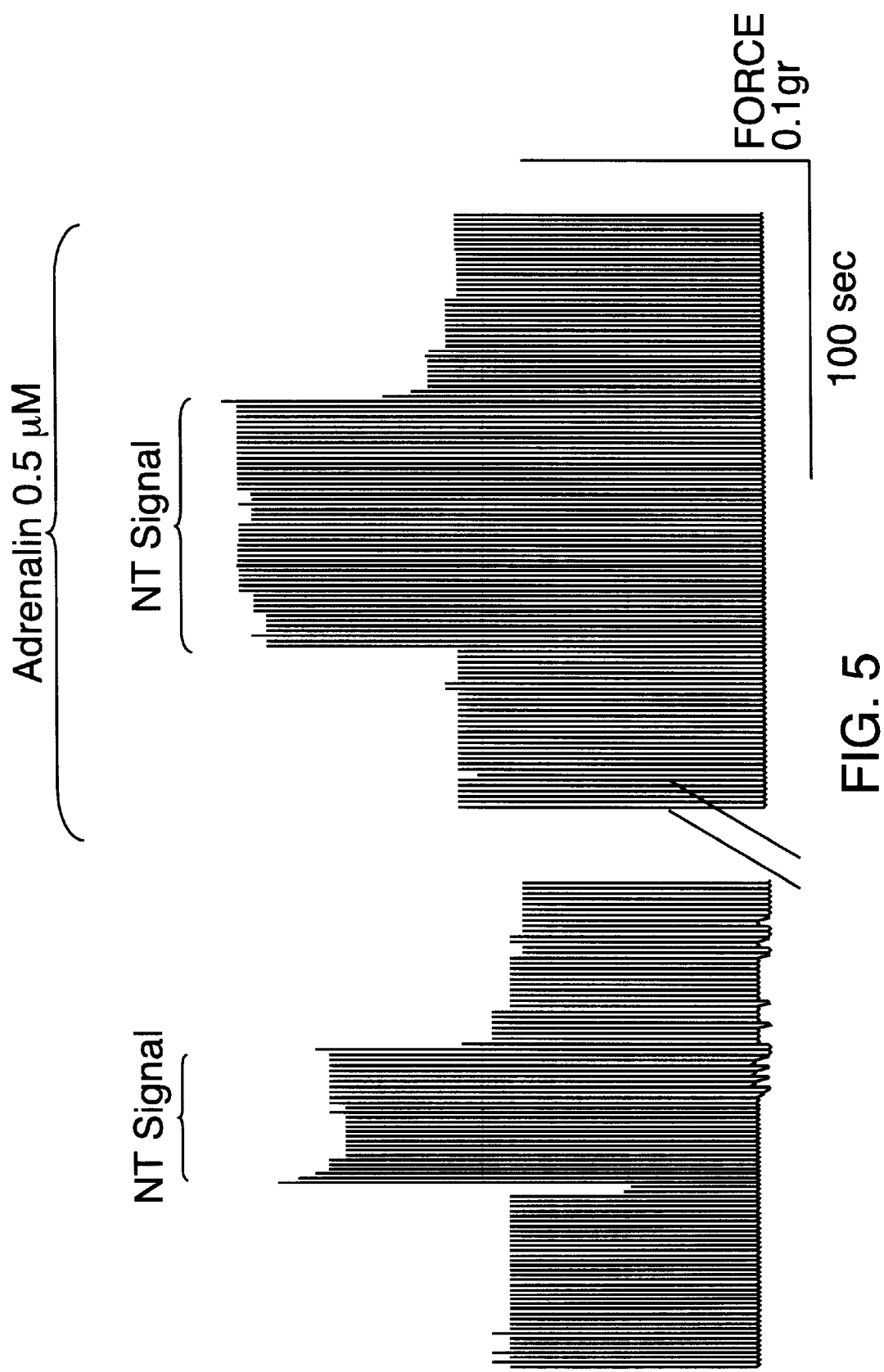
FIG. 5 shows the effect of the application of an NT-signal to a rabbit papillary muscle in the presence of adrenaline.

An experiment was carried out on a rabbit papillary muscle, in the presence of adrenaline, and the results are shown in FIG. 5. This graph is composed from two different triles on the same papillary muscle (left, rabbit). In the control turning on the NT signal caused an increase of about 110%, then adrenaline, 0.5 µM was added to the perfusion chamber. The recording shown in FIG. 5 (on the right) was taken after 5 minutes perfusion with adrenaline. Adrenaline caused a 20% increase in the basal contraction force of the muscle. When the NT signal was turned on there was an additional 86% increase in the peak contraction force. This result indicates that high adrenaline concentration does not attenuate the increase in muscle contraction after NT signal stimulation.

Parameters:
 Pacing: 1 Hz, 2 mS duration, 3 mA
 NT signal was: 30 mS delay, 60 mS duration, 6 mA.

EXAMPLE 6

Stimulation in the Presence of Diltiazem

Figure 6:
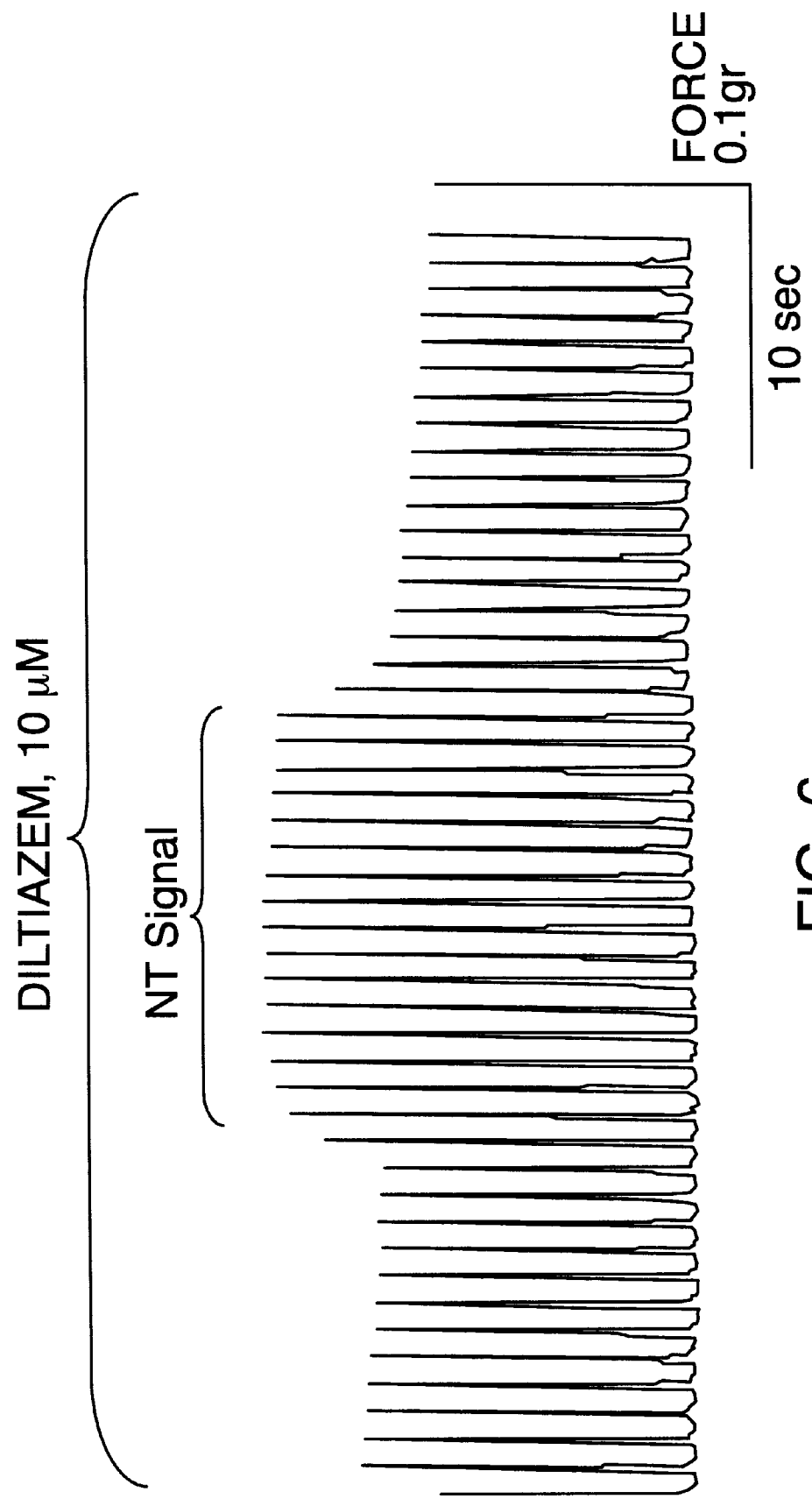
FIG. 6 shows the effect of the application of an NT-signal to a rabbit papillary muscle in the presence of Diltiazem.

An experiment was carried out on a rabbit papillary muscle, in the presence of Diltiazem (a Ca-channel blocker commonly used in clinical treatment in ischemic heart disease), and the results are shown in FIG. 6.

A rabbit papillary muscle was stimulated in Organ-Bath perfused by KRS and 10 µM Diltiazem, (Lot 702663). The NT-signal applied to this preparat produced an average increase in peak force of 20% under these experimental conditions. The drug caused a significant reduction in the basal contraction force of the muscle.

Parameters:
 Pacing: 1 Hz, 2 mS Duration, 1 mA.
 NT Signal: 50 mS Delay, 50 mS Duration, 4 mA.
 Temp. 36.2° C.

EXAMPLE 7

Stimulation in the Presence of Digoxin

Figure 7:
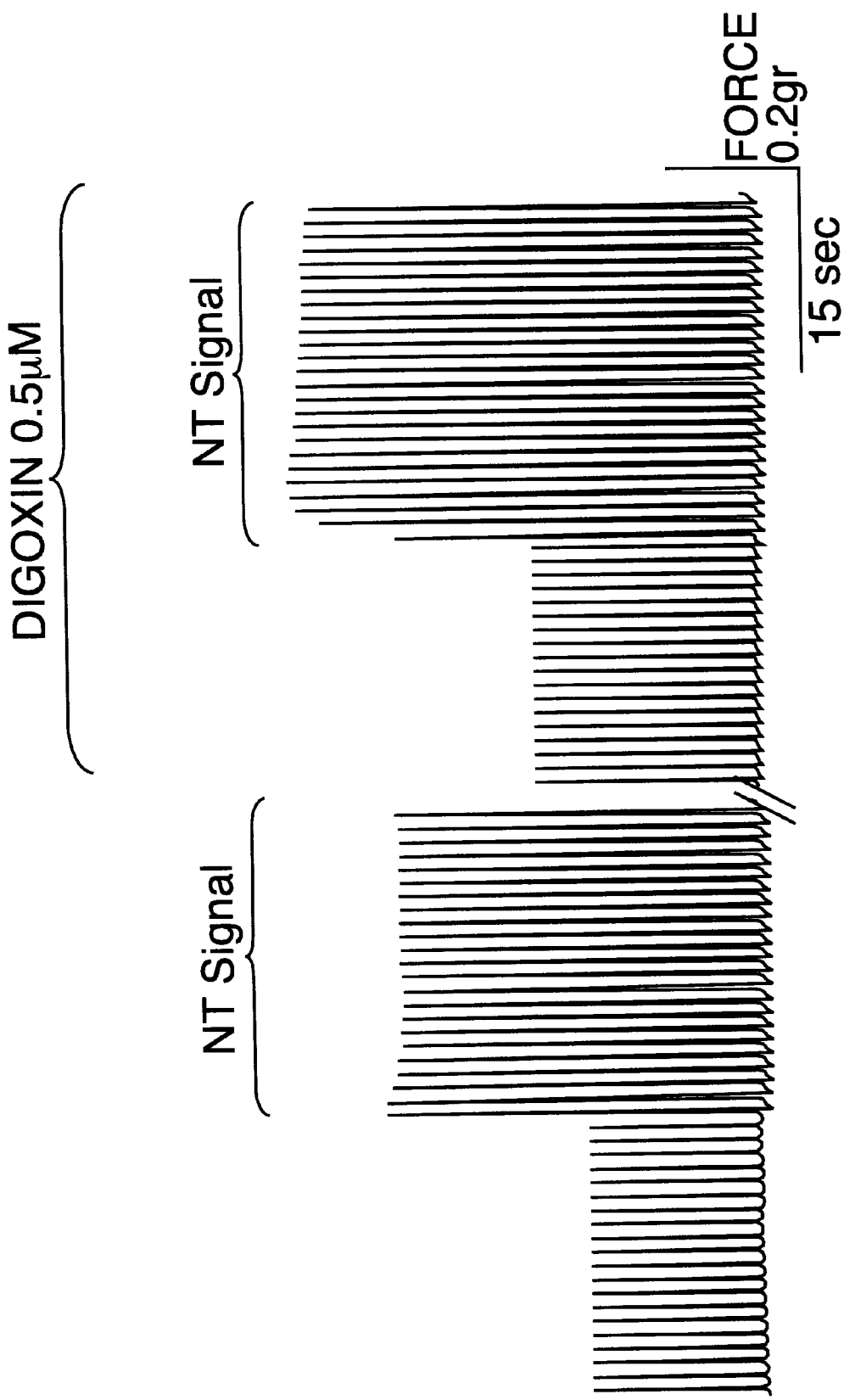
FIG. 7 shows the effect of the application of an NT-signal to a rabbit papillary muscle in the presence, of Digoxin.

An experiment was carried out on a rabbit papillary muscle, in the presence of Digoxin, and the results are shown in FIG. 7.

There is a 115% increase in the NT-signal induced force on the control without the addition of the drug. Addition of Digoxin caused an increase of 38% of the basal contraction force. Applying the NT-signal on the Digoxin-treated muscle caused a further increase of 86% on the new basal level, after 19 minutes treatment with Digoxin The combined Digoxin-NT signal treatment is synergistic, and the increase in muscle contraction, as compared to the single contributions of each treatment, is 20%, as shown in the graph.

Pacing: 1 Hz, 2 mS, 3 mA.
NT Signal: 1 Hz, delay 30 mS, duration 60 mS.

Referring now to FIG. 8, a schematic representation of an apparatus according to one embodiment of the invention is seen. In this scheme, a portion of a cardiac muscle, H, is brought into closed positioned relationship with two electrodes, E1 and E2, the ends of which are positioned at root position R1 and R2, respectively. The electrodes receive the voltage and current from a signal generator S, the construction of which is conventional and well know to skilled persons, and which is therefore not described here in detail, which in turn receives power from a power line, PL, connected to an autonomous power source or to the mains, as the case may be. The activity of the power signal generator S is controlled by a controller, C, which may be a microprocessor, or which may be an external controlling device, e.g., a PC or the like computer. The controller C controls the parameters of the signal generated by the signal generator, such as current intensity, frequency and timing, and may use both preset parameters (e.g., the frequency of pulse generation) and feedback input, e.g., from apparatus which monitors heart or other parameters, or from a pace maker which supplies the pacing signal. These input signals are collectively schematically indicated in the figure as FB. Of course, the apparatus is only schematically shown, for the sake of brevity. And the skilled person will easily be able to devise many different kinds of apparatus suitable to supply the signal needed in carrying out the invention.

All the above description and examples have been given for the purpose of illustration and are not intended to limit the invention in any way. Many modifications, can be carried out in the invention: for instance, many different drugs can be used in conjunction with an NT-signal, or different combinations of drugs can be used; furthermore, different signals can be employed, all without exceeding the scope of the invention.

What is claimed is:

1. A method for the combined drug/electric stimulation treatment of a cardiac muscle, comprising a) administering to a patient in need thereof a drug which affects the cardiovascular system and which affects the cardiac muscle, or a mixture of two or more such drugs, b) creating a non-excitatory electric potential between at least two points located in the vicinity of the muscle, and c) controlling one or more of the parameters consisting of start time, duration, magnitude and polarity of the non-excitatory electric potential created between said at least two points.

2. A method for the combined drug/electric stimulation treatment of a cardiac muscle, comprising a) administering to a patient in need thereof a drug which affects the cardiovascular Stem and which affects the cardiac muscle, or a mixture of two or more such drugs, b) causing a non-excitatory electric current to flow between at least two points located in the vicinity of the muscle, and c) controlling one or more of the parameters consisting of start time, duration, magnitude and polarity of the non-excitatory electric current flowing between said at least two points.

3. A method according to claim 2, wherein the non-excitatory electric current is a DC current.

4. A method according to claim 3, further comprising generating a complex signal by superimposing on the DC signal one or more waveforms of given frequency and amplitude.

5. A method according to any one of claims 2 to 4, wherein the flow of the non-excitatory DC electric current is synchronized to heart activity.

6. A method according to claim 5, wherein the non-excitatory DC electric current flows not at every beat of the heart.

7. A method according to claim 6, wherein the non-excitatory DC electric current flows every 1, 2 or 3 beats of the heart.

8. A method for the combined drug/electric-stimulation treatment of a cardiac muscle, comprising:
   administering to a patient in need thereof a drug which affects the cardiovascular system and which affects the cardiac muscle, or a mixture of two or more such drugs;
   providing means for creating an electric potential between at least two points located in the vicinity of the cardiac muscle;
   providing means for causing a non-excitatory electric current to flow between said at least two point; and
   controlling the start time, duration and magnitude of the electric current flowing between said at least two points so as to impart a desired change in cardiac muscle contractility.

9. A method according to any one of claims 1, 2, and 8, wherein the change in cardiac muscle contractility is designed at least partially to compensate for cardiac muscle contractility decrease induced by said drug or mixture of drugs.

10. A method according to any one of claims 1, 2, and 8, wherein the change in cardiac muscle contractility is designed at least partially to compensate for cardiac muscle contractility increase induced by said drug or mixture of drugs.

11. A method according to any one of claims 1, 2, and 8, wherein the change in cardiac muscle contractility is designed to add to and/or amplify the cardiac muscle contractility increase or decrease induced by said drug or mixture of drugs.

12. A method according to any one of claims 1, 2, and 8, for reducing the dosage of a cardiovascular drug which affects cardiac muscle contractility.

13. A method according to any one of claims 1, 2, and 8, for reducing the dosage of a cardiovascular drug which affects the electrophysiological characteristics of the cardiac muscle.

14. A method for the combined drug/electric-stimulation treatment of a cardiac muscle, comprising:
   administering to a patient in need thereof a drug which affects the cardiovascular system and which affects the cardiac muscle, or a mixture of two or more such drugs;
   providing an electric potential between at least a pair of electrodes in the vicinity of the cardiac muscle at at least two root locations;
   causing a non-excitatory electric current to flow between said at least two contacting locations; and
   controlling the start time, duration and magnitude of the electric current flowing between said at least two root locations, so as to impart the desired change in cardiac muscle contractility.

15. A method according to claim 14, wherein the means for causing a non-excitatory electric current to flow, are synchronized to heart activity.

16. A method according to claim 15, wherein the means for causing a non-excitatory electric current to flow operate not at every beat of the heart.

17. A method according to claim 16, wherein the means for causing a non-excitatory electric current to flow operate every 1, 2 or 3 beats of the heart.

18. Apparatus for the combined drug/electric-stimulation treatment of a cardiac muscle, comprising:
   means for creating an electric potential between at least two points located in the vicinity of the cardiac muscle;
   means for causing a non-excitatory electric current to flow between said at least two points;
   means for controlling the start time, duration and magnitude of the electric current flowing between said at least two points; and
   means for superimposing on the DC signal one or more waveforms of given frequency and amplitude, thereby to generate a complex signal.

19. Apparatus according to claim 20, comprising:
   means for creating an electric potential between at least a pair of electrodes in the vicinity of the cardiac muscle at at least two root locations;
   means for causing a non-excitatory electric current to flow between said at least two root locations;
   means for controlling the start time, duration and magnitude of the electric current flowing between said at least two root locations; and
   means for superimposing on the DC signal one or more waveforms of given frequency and amplitude, thereby to generate a complex signal.

* * * * *

(12) EX PARTE REEXAMINATION CERTIFICATE (6888th)
United States Patent
Ben-Haim et al.

(10) Number: US 6,236,887 C1
(45) Certificate Issued: Jun. 23, 2009

(54) DRUG-DEVICE COMBINATION FOR CONTROLLING THE CONTRACTILITY OF MUSCLES

(75) Inventors: Shlomo Ben-Haim, Haifa (IL); Nissim Darvish, Haifa (IL); Yuval Mika, Haifa (IL); Maier Fenster, Petach Tikva (IL)

(73) Assignee: Impulse Dynamics N.V., Curacao (NL)

Reexamination Request:
No. 90/008,707, Jun. 13, 2007

Reexamination Certificate for:
Patent No.: 6,236,887
Issued: May 22, 2001
Appl. No.: 09/254,993
Filed: Mar. 12, 1999

(22) PCT Filed: Jul. 9, 1997
(86) PCT No.: PCT/IL97/00232
§ 371 (c)(1), (2), (4) Date: Mar. 12, 1999
(87) PCT Pub. No.: WO98/10829
PCT Pub. Date: Mar. 19, 1998

Related U.S. Application Data
(60) Provisional application No. 60/026,392, filed on Sep. 16, 1996, now abandoned.

(51) Int. Cl.
*A61N 1/00* (2006.01)
*A61N 1/365* (2006.01)

(52) U.S. Cl. .................... 607/3; 607/68; 607/9
(58) Field of Classification Search .................. None
See application file for complete search history.

(56) References Cited
U.S. PATENT DOCUMENTS

| | | |
|---|---|---|
| 3,572,345 A | 3/1971 | Auphan |
| 3,587,567 A | 6/1971 | Schiff |
| 3,651,805 A | 3/1972 | Breiling |
| 3,651,806 A | 3/1972 | Hirshberg |
| 3,933,147 A | 1/1976 | Du Vall et al. |
| 3,942,536 A | 3/1976 | Dahl et al. |
| 3,952,750 A | 4/1976 | Mirowski et al. |
| 4,030,509 A | 6/1977 | Heilman et al. |
| 4,106,494 A | 8/1978 | McEachern |
| 4,164,216 A | 8/1979 | Person |

(Continued)

FOREIGN PATENT DOCUMENTS

| | | |
|---|---|---|
| EP | 0148687 | 7/1985 |
| EP | 0314078 | 5/1989 |
| EP | 0314078 B1 | 10/1993 |
| EP | 0727241 | 8/1996 |
| EP | 0 727 241 A1 | 8/1996 |

(Continued)

OTHER PUBLICATIONS

M. Inoue, et al., "Summation and Inhibition by Ultrarapid Train Pulses in Dogs: Effects of Frequency and Duration of Trains, Lidocaine, and Beta Blockade," Pacing Clin. Electrophysiol., vol. 12, iss. 11, pp. 1777–1786 (Nov. 1989).

Y.I. Zilberter, et al., "Open Na+ Channel Blockade: Multiple Rest States Revealed by Channel Interactions with Disopyramide and Quinidine," Am. J. Physiol., vol. 266, iss. 5 pt. 2, pp. H2007–17 (May 1994).

(Continued)

*Primary Examiner*—Beverly M. Flanagan

(57) ABSTRACT

An apparatus for the combined drug/electric-stimulation treatment of a cardiac muscle comprises circuitry (S) for creating a non-excitatory electric potential between at least two points (R1, R2) located in the vicinity of a muscle (H). A method for the combined drug/electric-stimulation treatment of a cardiac muscle, using the apparatus, involves controlling the start time, duration, and magnitude of the electric current flowing between said at least two points, to impart a desired change in cardiac muscle performance.

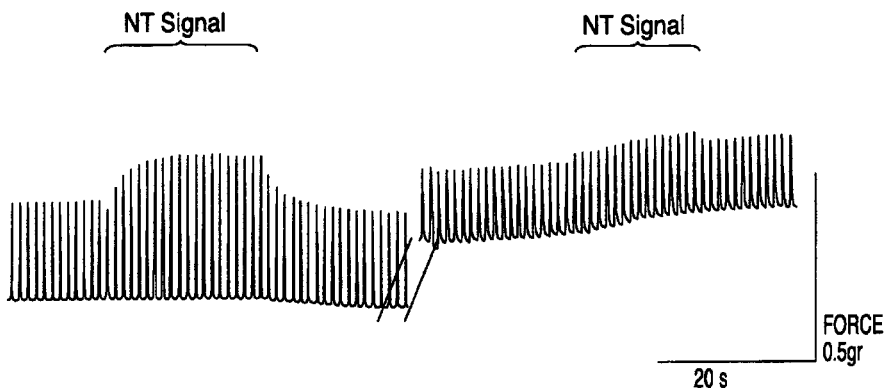

U.S. PATENT DOCUMENTS

| | | |
|---|---|---|
| 4,184,493 A | 1/1980 | Langer et al. |
| 4,202,340 A | 5/1980 | Langer et al. |
| 4,223,678 A | 9/1980 | Langer et al. |
| 4,237,895 A | 12/1980 | Johnson |
| 4,273,114 A | 6/1981 | Barkalow et al. |
| 4,312,354 A | 1/1982 | Walters |
| 4,316,472 A | 2/1982 | Mirowski et al. |
| 4,337,776 A | 7/1982 | Daly et al. |
| 4,384,585 A | 5/1983 | Zipes |
| 4,387,717 A | 6/1983 | Brownlee et al. |
| 4,403,614 A | 9/1983 | Engle et al. |
| 4,407,288 A | 10/1983 | Langer et al. |
| 4,411,268 A | 10/1983 | Cox |
| 4,440,172 A | 4/1984 | Langer |
| 4,506,680 A | 3/1985 | Stokes |
| 4,543,956 A | 10/1985 | Herscovici |
| 4,554,922 A | 11/1985 | Prystowsky et al. |
| 4,559,946 A | 12/1985 | Mower |
| 4,566,456 A | 1/1986 | Koning et al. |
| 4,572,191 A | 2/1986 | Mirowski et al. |
| 4,628,934 A | 12/1986 | Pohndorf et al. |
| 4,651,716 A | 3/1987 | Forester et al. |
| 4,674,508 A | 6/1987 | DeCote |
| 4,679,572 A | 7/1987 | Baker, Jr. |
| 4,690,155 A | 9/1987 | Hess |
| 4,726,279 A | 2/1988 | Kepler et al. |
| 4,726,379 A | 2/1988 | Altman et al. |
| 4,765,341 A | 8/1988 | Mower et al. |
| 4,830,006 A | 5/1989 | Haluska et al. |
| 4,928,688 A | 5/1990 | Mower |
| 4,979,507 A | 12/1990 | Heinz et al. |
| 4,998,531 A | 3/1991 | Bocchi et al. |
| 5,002,052 A | 3/1991 | Haluska |
| 5,003,976 A | 4/1991 | Alt |
| 5,020,544 A | 6/1991 | Dahl et al. |
| 5,022,396 A | 6/1991 | Watanabe |
| 5,026,397 A | 6/1991 | Aoki et al. |
| 5,044,375 A | 9/1991 | Bach, Jr. et al. |
| 5,083,564 A | 1/1992 | Scherlag |
| 5,085,218 A | 2/1992 | Heil, Jr. et al. |
| 5,087,243 A | 2/1992 | Avitall |
| 5,097,832 A | 3/1992 | Buchanan |
| 5,097,843 A | 3/1992 | Soukup et al. |
| 5,111,815 A | 5/1992 | Mower |
| 5,129,394 A | 7/1992 | Mehra |
| 5,137,021 A | 8/1992 | Wayne et al. |
| 5,156,147 A | 10/1992 | Warren et al. |
| 5,156,149 A | 10/1992 | Hudrlik |
| 5,161,527 A | 11/1992 | Nappholz et al. |
| 5,163,428 A | 11/1992 | Pless |
| 5,199,428 A | 4/1993 | Obel et al. |
| 5,205,284 A | 4/1993 | Freeman |
| 5,213,098 A | 5/1993 | Bennett et al. |
| 5,231,988 A | 8/1993 | Wernicke et al. |
| 5,236,413 A | 8/1993 | Feiring |
| 5,282,785 A | 2/1994 | Shapland et al. |
| 5,284,491 A | 2/1994 | Sutton et al. |
| 5,286,254 A | 2/1994 | Shapland et al. |
| 5,305,745 A | 4/1994 | Zacouto |
| 5,320,543 A | 6/1994 | Roline et al. |
| 5,320,642 A | 6/1994 | Scherlag |
| 5,320,643 A | 6/1994 | Roline et al. |
| 5,324,327 A | 6/1994 | Cohen |
| 5,327,887 A | 7/1994 | Nowakowski |
| 5,346,506 A | 9/1994 | Mower et al. |
| 5,353,800 A | 10/1994 | Pohndorf et al. |
| 5,366,486 A | 11/1994 | Zipes et al. |
| 5,368,040 A | 11/1994 | Carney |
| 5,370,665 A | 12/1994 | Hudrlik |
| 5,386,835 A | 2/1995 | Sterzer |
| 5,386,837 A | 2/1995 | Sterzer |
| 5,387,419 A | 2/1995 | Levy et al. |
| 5,391,192 A | 2/1995 | Lu et al. |
| 5,391,199 A | 2/1995 | Ben-Haim |
| 5,398,683 A | 3/1995 | Edwards et al. |
| 5,411,531 A | 5/1995 | Hill et al. |
| 5,415,629 A | 5/1995 | Henley |
| 5,417,717 A | 5/1995 | Salo et al. |
| 5,419,763 A | 5/1995 | Hildebrand |
| 5,425,363 A | 6/1995 | Wang |
| 5,433,730 A | 7/1995 | Alt |
| 5,443,485 A | 8/1995 | Housworth et al. |
| 5,445,609 A | 8/1995 | Lattin et al. |
| 5,447,520 A | 9/1995 | Spano et al. |
| 5,458,568 A | 10/1995 | Racchini et al. |
| 5,464,020 A | 11/1995 | Lerner |
| 5,468,254 A | 11/1995 | Hahn et al. |
| 5,472,453 A | 12/1995 | Alt |
| 5,476,484 A | 12/1995 | Hedberg |
| 5,476,485 A | 12/1995 | Weinberg et al. |
| 5,476,497 A | 12/1995 | Mower et al. |
| 5,482,052 A | 1/1996 | Lerner |
| 5,499,971 A | 3/1996 | Shapland et al. |
| 5,501,662 A | 3/1996 | Hofmann |
| 5,514,162 A | 5/1996 | Bornzin et al. |
| 5,520,642 A | 5/1996 | Bigagli et al. |
| 5,531,764 A | 7/1996 | Adams et al. |
| 5,540,722 A | 7/1996 | Clare et al. |
| 5,556,421 A | 9/1996 | Prutchi et al. |
| 5,568,809 A | 10/1996 | Ben-haim |
| 5,571,143 A | 11/1996 | Hoegnelid et al. |
| 5,578,061 A | 11/1996 | Stroetmann et al. |
| 5,584,803 A | 12/1996 | Stevens et al. |
| 5,584,804 A | 12/1996 | Klatz et al. |
| 5,584,868 A | 12/1996 | Salo et al. |
| 5,587,200 A | 12/1996 | Lorenz et al. |
| 5,601,609 A | 2/1997 | Duncan |
| 5,601,611 A | 2/1997 | Fayram et al. |
| 5,622,687 A | 4/1997 | Krishnan et al. |
| 5,626,622 A | 5/1997 | Cooper |
| 5,634,895 A | 6/1997 | Igo et al. |
| 5,634,899 A | 6/1997 | Shapland et al. |
| 5,649,966 A | 7/1997 | Noren et al. |
| 5,651,378 A | 7/1997 | Matheny et al. |
| 5,674,251 A | 10/1997 | Combs et al. |
| 5,674,259 A | 10/1997 | Gray |
| 5,683,431 A | 11/1997 | Wang |
| 5,687,734 A | 11/1997 | Dempsey et al. |
| 5,713,935 A | 2/1998 | Prutchi et al. |
| 5,720,768 A | 2/1998 | Verboven-Nelissen |
| 5,735,876 A | 4/1998 | Kroll et al. |
| 5,738,096 A | 4/1998 | Ben-Haim |
| 5,738,105 A | 4/1998 | Kroll |
| 5,749,906 A | 5/1998 | Kieval et al. |
| 5,755,740 A | 5/1998 | Nappholz |
| 5,782,876 A | 7/1998 | Flammang |
| 5,782,881 A | 7/1998 | Lu et al. |
| 5,792,198 A | 8/1998 | Nappholz |
| 5,792,208 A | 8/1998 | Gray |
| 5,797,967 A | 8/1998 | KenKnight |
| 5,800,464 A | 9/1998 | Kieval |
| 5,807,234 A | 9/1998 | Bui et al. |
| 5,807,306 A | 9/1998 | Shapland et al. |
| 5,814,079 A | 9/1998 | Kieval |
| 5,865,787 A | 2/1999 | Shapland et al. |
| 5,871,506 A | 2/1999 | Mower |
| 5,906,607 A | 5/1999 | Taylor et al. |
| 5,913,876 A | 6/1999 | Taylor et al. |
| 5,927,284 A | 7/1999 | Borst et al. |
| 6,006,134 A | 12/1999 | Hill et al. |
| 6,032,074 A | 2/2000 | Collins |

| | | | |
|---|---|---|---|
| 6,032,672 A | 3/2000 | Taylor |
| 6,041,252 A | 3/2000 | Walker et al. |
| 6,067,470 A | 5/2000 | Mower |
| 6,071,305 A | 6/2000 | Brown et al. |
| 6,086,582 A | 7/2000 | Altman et al. |
| 6,136,019 A | 10/2000 | Mower |
| 6,141,586 A | 10/2000 | Mower |
| 6,141,587 A | 10/2000 | Mower |
| 6,151,586 A | 11/2000 | Brown |
| 6,178,351 B1 | 1/2001 | Mower |
| 6,295,470 B1 | 9/2001 | Mower |
| 6,317,631 B1 | 11/2001 | Ben-Haim et al. |
| 6,337,995 B1 | 1/2002 | Mower |
| 6,341,235 B1 | 1/2002 | Mower |
| 6,343,232 B1 | 1/2002 | Mower |
| 6,411,847 B1 | 6/2002 | Mower |
| 6,415,178 B1 | 7/2002 | Ben-Haim et al. |
| 6,558,345 B1 | 5/2003 | Houben et al. |

FOREIGN PATENT DOCUMENTS

| | | |
|---|---|---|
| JP | S62-275471 | 11/1987 |
| JP | 04117967 | 4/1992 |
| JP | 4365493 | 12/1992 |
| JP | 7126600 | 5/1995 |
| JP | 8243176 | 8/1996 |
| WO | WO 91/19534 | 12/1991 |
| WO | WO 92/00716 | 1/1992 |
| WO | WO 93/18820 | 9/1993 |
| WO | WO 94/17855 | 8/1994 |
| WO | WO 95/08316 | 3/1995 |
| WO | WO 97/25098 | 7/1997 |
| WO | WO 97/25101 | 7/1997 |
| WO | WO 98/10828 | 3/1998 |
| WO | WO 98/10829 | 3/1998 |
| WO | WO 98/10830 | 3/1998 |
| WO | WO 98/10831 | 3/1998 |
| WO | WO 98/10832 | 3/1998 |
| WO | WO 99/03533 | 1/1999 |
| WO | WO 99/09971 | 3/1999 |
| WO | WO 00/04947 | 2/2000 |
| WO | WO 00/27475 | 5/2000 |
| WO | WO 00/42914 | 7/2000 |
| WO | WO 00/53257 | 9/2000 |
| WO | WO 00/74773 A1 | 12/2000 |
| WO | WO 01/49367 | 7/2001 |
| WO | WO 01/52931 | 7/2001 |
| WO | WO 01/66183 | 9/2001 |
| WO | WO 01/91854 | 12/2001 |
| WO | WO 01/93950 A1 | 12/2001 |
| WO | WO 01/93951 A1 | 12/2001 |

OTHER PUBLICATIONS

G. Stark, et al., "How to Measure AV Nodal Refractoriness in the Presence of Verapamil, Mmiodarone, Digoxin, and Diltiazen," Pacing Clin. Electrophysiol., vol. 19. iss. 2, pp. 157–164 (Feb. 1996).

D.E. Euler, et al., "Acetylcholine Release by a Stimulus Train Lowers Atrial Fibrillation Threshold," Am. J. Physiol., vol. 253, iss. 4 part 2, pp. H863–8 (Oct. 1987).

Paul, VE., et al. "Automatic Recognition of Ventricular Arrythmias Using Temporal Electrogram Anaylsis" Pace, vol. 14, pp. 1265–1273, (1991).

Qiuzhen Xue et al., "Neural–Network–Based Adaptive matched Filtering for QRS Detection", IEEE Transactions on Biomedical Engineering, vol. 39, No. 4, Apr. 1992.

Sweeny RJ, et al., abstract of "Countershock Strength–Duration Relationship for Myocardial Refractory Period Extension", Acad Emerg. Med., Jan. 1995, vol. 2, No. 1, pp. 57–62.

Sweeny RJ, et al., abstract of "Refractory Interval After Transcardiac Shocks During Ventricular Fibrillation", Circulation, Dec. 1996, vol. 94, No. 11, pp. 2947–2952.

Sweeny RJ, et al., abstract of "Ventricular Refractory Period Extension Caused by Defibrillation Shocks", Circulation, Sep. 1990, vol. 82, No. 3, pp. 965–972.

Soria, et al., "Cytosolic Calcium Oscillations And Insulin Release in Pancreatic Islets Of Langerhans", Diabetes & Metabolism (Paris), 1998, 24, pp. 37–40.

Gomis, et al., "Oscillatory Patterns of Electrical Activity in Mouse Pancreataic Islets Of Langerhans Recorded in Vivo", Pflugers ARch—Eur J. Physiol (1986) 432, Springer–Verlag 1996, pp. 510–515.

Todd, et al., Subcutaneous Glucagon–Like Peptide I Improves Postprandial Glycaemic Contori Over A 3–Week Period in Patients With Early Type 2 Diabetes, Clinical Science (1998) 95, pp. 325–329.

Tian Y. Tsong, Electroporation Of Cell Membranes, Biophysical Journal, vol. 60, Aug. 1991, pp. 297–306.

Mercando, et al., Automated Detection Of Tachycardias By Antitachycardia Devices, Therapy, Chapter 100, pp. 943–948.

Hoffman, B.F. et al., "Effects of Postextrasystolic Potentiation on Normal & Failing Hearts", Bulletin of New York Academy of Medicine, 41 in 1965, pp. 498–534.

King, A. et al., The Inotropic Action of Paired Pulse Stimulation in the Normal and Failing Heart: An Experimental Study, Cardiovascular Research, vol. 2, Apr. 1968, pp. 122–129.

Knisley et al., "Prolgongation and Shortening of Action Potentials by Electrical Shocks in Frog Venticular Muscle", American Journal of Physiology 6 (Heart Circ. Physiol. 35, 1994) pp. H2348–H2358.

Koller, et al., "Relation between Rapolarization and Refractoriness During Programmed Electrical Stimulation in the Human Ventricle", Circulation 91(9), 2378–2384, 1995.

Fu, et al., System Identification Of Electrically Coupled Smooth Muscles Cells: The Passive Electrical Properties, IEEE Transactions On Biomedical Engineering, vol. 38, No. 11, Nov. 1991.

Schirra et al., "Mechanisms Of The Antidiabetic Action Of Subcutaneous Glucagon–Like Peptide–1 (17–36)amide in Non–Insulin Dependent Diabetes Mellitus", Journal Of Endocrimology Ltd. 1998 156, jpages. 177–186.

Palti, et al., "Islets Of Langerhans Generate Wavelike Electric Activity Modulated By Glucose Concentration", Diabetes, vol. 45, May 1996, pp. 595–601.

Knisley, et al., "Effect Of Field Stimulation On Cellular Repolarization In Rabbit Myocardium", Circulation Research, vol. 70, No. 4, Apr. 1992, pp. 707–715.

Pumir et al., "Control Of Rotating Waves In Cardiac Muscle: Analysis Of The Effect Of An Electrif Field", 1994, The Royal Society, 257, pp. 129–134.

Homer et al. Electrode For Recording Direction Of Activation, Conduction Velocity, And Monophasic Action Potential Of Myocardium, The American Physiological Society, 1997, pp. H1917–H1927.

Antoni, H. et al. "Polarization Effects of Sinusoidel 50–Cycle Alternating Current on Membrane Potential of Mammalian Cardiac Fibers", Pfluegers Arch. 314, pp. 274–291 (1970).

Bakker, P.F., et al., "Biventricular Pacing Improves Functional Capacity in Patients with End–Stage Congestive Heart Failure" PACE, vol. 17, Apr. 1995, Part 11, one page.

Bargheer K. et al., "Prolongation of Monophasic Action Potential Duration and the Refractory Period in the Human Heart by Tedisamil, a New Potassium–Blocking Agent", J. Eur Heart 15 (10), Oct. 1994, pp. 1409–1414.

Sakuma, et al., "A Model Analysis Of Aftereffects Of High–Intensity DC Stimulation On Action Potential Of Ventricular Muscle", IEEE Transactions On Biomedical Engineering, vol. 45, No. 2, Feb. 1998.

Lindstrom et al., "Intracellular Calcium Oscillations In A T–Cell Line After Exposure To Extremely–Low–Frequency Magnetic Fields With Variable Frequencies And Flux Densities", Bioelectromagnetics 16:41, p. 41–47.

Eroi–Yimaz, et al., "Reversed Remodelling Of Diated Left Sided Cardiomyopathy After Upgrading From VVIR to VVIR biventicular Pacing", Elsevier Science Ltd., on behalf of The European Society of Cardiology, 2002, vol. 4, pp. 445–449.

M. Yokoyama, "The Phase Of Supernormal Excitation In Relation To The Strength Of Subthreshold Stimuli", Heart Institute Of Japan, Jun. 1975, pp. 315–325.

Cheng, et al., "Calcium Sparks: Elementary Events Underlying Excitation–Contraction Coupling In Heart Muscle" Science, vol. 262, Oct. 29, 1993, pp. 740–744.

Coulton et al., "Magnetic Fields And Intracellular Calcium: Effects On Lymphocytes Exposed To Conditions For Cyclotron Resonance"., Phys. Med. Biol., 38, (1993), pp. 347–360.

Taniguchi, et al., "Inhomogeneity Of Cellular Activation Time And VMax In Normal Myocardial Tissue Under Electrical Field Stimulation"., American Physiological Society 1994, pp. H694–H705.

Talit, U. et al., "The Effects of External Cardiac Pacing on Stroke Volume", Pace 13, May 1990, pp. 598–560.

Wessale, J.L. et al., "Stroke Volume and Three Phase Cardiac Output Rate Relationship with Ventricular pacing" Pace 13, May 1990, pp. 673–680.

Wirtzfeld, A. et al., "Physiological Pacing: Present Status and Future Developments", Pace 10 Jan.–Feb. 1987, Part I, pp. 41–57.

Gill, et al., "Refactory Period Extension During Ventricular Pacing At Fibrillatory Pacing Rates", PACE, vol. 20, Mar. 1997, Part I, p. 647–653.

Franz, M.R., "Bridging TheGap BetweenBasic And Clinical Electrophysiology: What Can Be Learned From Monophasic Action Potential Recordings?", Journal Of Cardiovascular Electrophysiology, vol. 5, No. 8, Aug. 1994 pp. 699–710.

Foster, A.H., et al. "Acute Hemodymanic Effects of Atrio–Biventricular Pacing In Humans", The Society of Thoracic Surgeons 1995, pp. 294–300.

Jaremko, J, et al. "Advances Toward The Implantable Artificial Pancreas For Treatment Of Diabetes"; Diabetes Care, vol. 21, No. 3, Mar. 1998; pp. 444–450.

Bakker, P.F., et al.; Beneficial Effects Of Biventricular Pacing In Congestive Heart Failure, PACE, vol. 17, 1994, Part II.

Swerdlow, Charles, et al., "Cardiovascular Collapse Caused By Electrocardiographically Silent 60–Hz Intracardiac Leakage Current", American Heart Association, Inc. 1999.

Burfeind, W.R., et al., "The Effects Of Mechanical Cardiac Stabilization On Left Ventricular Performance", European Journal Of Cardio–Thoracic Surgery 14 (1998) pp. 285–298.

Thakor, N.V., et al., "Effect Of Varying Pacing Waveform Shapes On Propagation And Hemodynamics In The Rabbit Heart", American Journal Of Cardiology, vol. 79 (6A), Mar. 20, 1997, pp. 36–43.

Langberg, J.J., et al., "Identification Of Ventricular Tachycardia With Use Of The Morphology Of The Endocardial Electrogram", Circulation, vol. 77, No. 6, Jun. 1988 pp. 1363–1369.

Fleg, J.L., Impact Of Aage On the Cardiovascular Response To Dynamic Upright Exercise In Healthy Men And Women; pp. 890–900.

Fain, E.S., Improved Internal Defibrillation Efficacy With A Biphasic Waveform, American Heart Journal, vol. 117, No. 2, Feb. 1989 pp. 358–364.

Skale, B.T., et al., "Inhibition Of Premature Ventricular Extrastimuli By Subthreshold conditioning Stimuli", JACC, vol. 6, No. 1, Jul. 1985.

Franz, Michael R., "Method And Theory Of Monophasic Action Potential Recording", Cardiology Division, Stanford University School of Medicine, Stanford, CA., 1191, pp. 347–368.

Cazeau, S., et al., "Multisite Pacing For End–Stage Heart Failure: Early Experrience", PACE, Nov. 1996, Vo. 19, Part II, pp. 1748–1757.

Dillion, S.M., "Optical Recordings In The Rabbit Heart Show That Defibrillation Strength Shocks Prolong The Duration Of Depolarization And The Refractory Period", Department of Pharmacology, College of Physicians and Surgeons, Columbia University, NYC., vol. 69, No. 3, Sep. 1991.

Cooper, W.M., "Postextrasystolic Potentiation. Do We Really Know What It Means And How To Use It?", Division of Cardiology, University of Texas Health Center at Tyler, TX., vol. 88, No. 6, Dec. 1993, pp. 2962–2971.

Saihara, S., et al., "Summation Of Excitation With A Single Conditioning Stimulus In The Canine Heart", PACE, vol. 13, Jan. 1990, pp. 52–58.

Burfeind, W.R., "The Effects Of Mechanical Cardiac Stabilization On Left Ventricular Performance", European Journal Of Cardio–Thoracic Surgery, 14 (1998), pp. 285–289.

Fromer, M., et al., "Ultrarapid Subthreshold Stimulation For Termination Of Atrioventricular Node Reentrant Tachycardia", JACC, vol. 20, No. 4, Oct. 1992, pp. 879–883.

Dereduex, D., et al., "Uterine Electroymography: A Critical View", American Jounral Obstet Gynecol, Dec. 1993, pp. 1636–1651.

Antman et al. "Treatment of 150 Cases of Life–Threatening Digitalis Intoxication With Digoxin–Specific Fab Antibody Fragments", Circulation, 81(6): 1744–1752, 1990.

Antoni et al. "Polarization Effects of Sinusoidal 50–Cycle Alternating Current on Membrane Potential of Mammalian Cardiac Fibres", Pflügers Archiv European Journal of Physiology, 314(4):274–291. 1970. Abstract.

Bakker et al. "Beneficial Effects of Biventricular Pacing of Congestive Heart Failure", Pace, 17(Part II): 318, 1994.

Bargheer et al. "Prolongation of Monophasic Action Potential Duration and the Refractory Period in the Human Heart by Tedisamil, A New Potassium–Blocking Agent", Journal European Heart, 15(10): 1409–1414, 1994, Abstract.

Bers "Excitation Contraction Coupling and Cardiac Contractile Force", Internal Medicine, 237(2): 17, 1991, Abstract.

Borst et al. "Coronary Artery Bypass Gratting Without Cardiopulomonary Bypass and Without Interuption of Native Coronary Flow Using A Novel Anastomosis Site Restraining Device (Octupus)", Journal of the American College of Cardiology, 27(6): 1356–1364, 1996.

Cano et al. "Dose–Dependent Reversal of Dixogin–Inhibited Activity of an In–Vitro Na+K+ATPase Model by Digoxin–Specific Antibody", Toxicology Letters, 85(2): 107–1011, 1996.

Cazeau et al. "Multisite Pacing for End–Stage Heart Failure: Early Experience", Pacing and Clinical Electrophysiology, 19(11): 1748–1757, 1996, Abstract.

Cheng et al. "Calcium Sparks: Elementary Events Underlying Excitation–Contraction Coupling in Heart Muscle", Science, 262(5134): 740–744, 1993, Abstract.

Cooper "Postextrasystolic Potention. Do We Really Know What It Means and How to Use It?", Circulation, 88: 2962–2971, 1993.

Coulton et al. "Magnetic Fields and Intracellular Calcium; Effects on Lymphocytes Exposed to Conditions for 'Cyclotron Resonance'", Phys. Med. Biol., 38: 347–360, 1993, Abstract.

Dillion "Optial Recordings in the Rabbit Heart Show That Defibrillation Strength Shocks Prolong the Duration of Depolarization and the Refractory Period", Circulation Research, 69: 842–856, 1991.

Dillon "Synchronized Repolarization After Defibrillation Shocks. A Possible Component of the Defibrillation Process Demonstration by Optical Recordings in Rabbit Heart", Circulation, 85(5): 1865–1878, 1992.

Fain et al. "Improved Internal Defibrillation Efficacy With A Biphasic Waveform", American Heart Journal, 117(2): 358–364, 1989, Abstract.

Fleg et al. "Impact of Age on the Cardiovasvular Response to Dynamic Upright Exercise in Healthy Men and Women", Journal of Applied Physiologyl, 78: 890–900, 1995, Abstract.

Fleischhauer et al. "Electrical Resistances of Interstitial and Microvascular Space as Determinants of the Extracellular Electrical Field and Velocity of Propagation in Ventricular Myocardium", Circulation, 92: 587–594, 1995.

Foster et al. "Acute Hemodynamic Effects of Atrio—Biventricular Padng in Humans", The Society of Thoracic Surgeons, 59: 294–300, 1995, Abstract.

Franz "Bridging the Gap Between Basic Clinical Electrophysiology: What Can Be Learned From Monophasic Action Potential Recordings?", Journal Cardiovasc Electrophysiology, 5(8): 699–710, 1994, Abstract.

Franz "Method and Theory of Monophasic Action Potential Recording", Prog. Cardiovasc Dis, 33(6): 347–368, 1991.

Fromer et al. "Ultrarapid Subthreshold Stimulation for Termination of Atriventricular Node Reentrant Tachycardia", Journal of the American College Cardiology, 20: 879–883, 1992.

Fu et al. "System Identification of Electrically Coupled Smooth Music Cells: The Passive Electrically Coupled Smooth Muscle Cells: The Passive Electrical Properties", IEEE Transactions on Biomedical Engineering, 38(11): 1130–1140, 1991.

Gill et al. "Refractory Period Extension During Ventricular Pacing at Fibrillatory Pacing Rates", Pacing and Clinical Elctrophysiology, 20(3): 647–653, 1997, Abstract.

Ham et al. "Classification of Cardiac Arrhythmias Using Fuzzy Artmap", IEEE Transactions on Biomedical Engineering, 43(4): 425–429, 1996, Abstract.

Hoffman et al. "Effects of Postextrasystolic Potentiation on Normal and Failing Hearts", Bulletin of the New York Academy of Medicine, 41(5): 498–534, 1965.

Josephson "Clinical Cardiac Electrophysiology: Techniques and Interpertations", Lea & Febiger, 2nd Ed., 2 P., 1991.

King et al. "The Inotropic Action of Paired Pulse Stimulation in the Normal and Failing Heart: An Experimental Study", Cardiovascular Research, 2: 122–129, 1968.

Knisley et al. "Prolgongation and Shortening of Action Potentials by Electrical Shocks in Frog Ventricular Muscle", American Journal of Physiology, 266(6): H2348–H2358, 1994, Abstract.

Koller et al. "Relation Between Repolarization and Refractoriness During Programmed Electrical Stimulation in the Human Right Ventricle", Circulation, 91(9): 2378–2384, 1995, Abstract.

Langberg et al. "Identification of Ventricular Tachycardia with Use of the Morphology of the Endocardial Electrogram", Circulation, 77(6): 1363–1369, 1988.

Lindstrom et al. "Intracellular Calcium Oscillations in A T–Cell Line After Exposure to Extremely–Low–Frequency Magnetic Fields with Variable Frequencies and Flux Densities", Bioelectromagnetics, 16(1): 41–47, 1995, Abstract.

Matheny et al. "Vagus Nerve Stimulation as A Method to Temporarily Slow or Arrest the Heart", Annals of Thoracic Surgery, 63(6): 528–29, 1997, Abstract.

McVeigh et al. "Noninvasive Measurement of Transmural Gradients in Myocardial Strain With MR Imaging", Radiology, 180(3): 677, 679–684, 1991.

Mercando et al. "Automated Detection of Tachycardias by Antitachycardia Devices", Cardiac Electrophysiology: From Cell to Bedside, Chap. 100: 943–948, 2004.

Moran et al. "Digoxin–Specific Fab Fragments Impair Renal Function in the Rat", Journal of Pharmacy and Pharmacology, 46(10): 854–856, 1994, Abstract.

Morse et al. "A Guide to Cardiac Pacemakers, Defibrillators and Related Products".

Nannini et al. "Muscle Recruitment With Intrafascicular Electrodes",IEEE Transactions on Biomedical Engineering, 38: 769–776, 1991, Abstract.

Paul et al. "Automatic Recognition of Ventricular Arrhythmias Using Temporal Electrogram Analysis", PACE, 14: 1265–1273, 1991.

Pumir et al. "Control of Rotating Waves in Cardiac Muscle: Analysis of the Effect of Electric Fields", Proceedings: Biological Sciences, 257(1349): 129–134, 1994, Abstract.

Ranjan et al. "Electrical Stimulation of Cardiac Myocytes", Annals of Biomedical Engineering, 23(6): 812–821, 1995, Abstract.

Saksena et al. "Prevention of Recurrent Atrial Fibrillation With Chronic Dual–Site Right Atrial Pacing", Journal of the American College of Cardiology, 28(3): 687–694, 1996, Abstract.

Schwartz et al. "Exposure of Frog Hearts to CW or Amplitude–Modified VHF Fields: Selective Efflux of Calcium Ions at 16 Hz", Bioelectromagnetics, 11(4): 349–358, 1990, Abstract.

Shumaik et al. "Oleander Poisoning: Treatment With Digoxin–Specific Fab Antibody Fragments", Annals of Emergency Medicine, 17(7): 732–735, 1988.

Skale et al. "Inhibition of Premature Ventricular Extrastimuli by Subthreshold Conditioning Stimuli", J. Am. Coll. Cardiol., 6: 133–140, 1985, Abstract.

Sweeny et al. "Countershock Strength–Duration Relationship for Myocardial Refractory Period Extension", Academic Emergency Medicine, 2(1): 57–62, 1995, Abstract.

Sweeny et al. "Refractory Interval After Transcardiac Shocks During Ventricular Fibrillation", Circulation, 94(11): 2947–2952, 1996.

Sweeny et al. "Ventricular Refractory Period Extension Caused by Defibrillation Shocks", Circulation, 82(3): 965–972, 1990.

Talit et al. "The Effect of External Cardiac Pacing on Stroke Volume", pace, 13(5): 598–602, 1990, Abstract.

Taniguchi et al. "Inhomogeneity of Cellular Activation Time and Vmax in Normal Myocardial Tissue Under Electrical Field Stimulation", Am. J. Physiol., 267: H694–H705, 1994, Abstract.

Thakor et al. "Effect of Varying Pacing Waveform Shapes on Propagation and Hemodynamics in the Rabbit Heart", The Americal Journal of Cardiology, 79(6A): 36–43, 1997, Abstract.

Tsong "Electroporation of Cell Membranes", Biophysical Journal, 60: 297–306, 1991.

Verrier et al. "Electrophysiologic Basis for T Wave Alternans as An Index of Vulnerability to Ventricular Fibrillation", Journal of Cardiovascular Electrophysiology, 5(5): 445–461, 1994, Abstract.

Webster Design of Cardiac Pacemakers, IEEE Press, p. xi–xiii, 1995.

Wessale et al. "Stroke Volume and the Three Phase Cardiac Output Rate Relationship With Ventricular Pacing", PACE, 13: 673–680, 1990.

Windle et al. "Subthreshold Conditioning Stimuli Prolong Human Ventricular Refractoriness", Am. J. Cardiol., 57(6): 381–386, 1986, Abstract.

Wintzfeld et al. "Physiological Pacing: Present Status and Future Developments", Pace, 10(Part I): 41–57, 1987. Abstract.

Xue et al. "Neural–Network–Based Adaptive Matched Filtering for QRS Detection", IEEE Transactions on Biomedical Engineering, 39(4): 317–329, 1992, Abstract.

Zipes et al. "Cardiac Electrophysiology—From Cell to Bedside", Saunders Co., 4th Ed., 1990.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claim 18 is confirmed.

Claims 1–3, 5, 8, 9, 11–15 and 19 are determined to be patentable as amended.

Claims 4, 6, 7, 10, 16 and 17, dependent on an amended claim, are determined to be patentable.

New claims 20–30 are added and determined to be patentable.

1. A method for the combined drug/electric stimulation treatment of a cardiac muscle, comprising a) administering to a patient in need thereof a drug which affects the cardiovascular system and which affects the cardiac muscle, or a mixture of two or more such drugs, b) creating a non-excitatory electric potential between at least two points located in the vicinity of the muscle, and c) controlling one or more of the parameters consisting of start time, duration, magnitude and polarity of the non-excitatory electric potential created between said at least two points, *said controlling imparting a desired therapeutic change in a contractility of said cardiac muscle, wherein an effect of said drug or drugs on said muscle interacts with an effect of said non-excitatory potential.*

2. A method for the combined drug/electric stimulation treatment of a cardiac muscle, comprising a) administering to a patient in need thereof a drug which affects the cardiovascular [Stem] *system* and which affects the cardiac muscle, or a mixture of two or more such drugs, b) causing a non-excitatory electric current to flow between at least two points located in the vicinity of the muscle, and c) controlling one or more of the parameters consisting of start time, duration, magnitude and polarity of the non-excitatory electric current flowing between said at least two points, *said controlling imparting a desired therapeutic change in a contractility of said cardiac muscle, wherein an effect of said drug or drugs on said muscle interacts with an effect of said non-excitatory current.*

3. A method according to claim [2] *1*, wherein the non-excitatory electric [current is] *potential induces* a DC current flow.

5. A method according to any one of claims 2 to 4 *or 20–24*, wherein the [flow] *creation* of the non-excitatory *potential induces a* DC electric current [is] *that flows* synchronized to heart activity.

8. A method for the combined drug/electric-stimulation treatment of a cardiac muscle, comprising: administering to a patient in need thereof a drug which affects the cardiovascular system and which affects the cardiac muscle, or a mixture of two or more such drugs;

providing means for creating an electric potential between at least two points located in the vicinity of the cardiac muscle;

providing means for causing a non-excitatory electric current to flow between said at least two point; and controlling the start time, duration and magnitude of the electric current flowing between said at least two points so as to impart a desired change in cardiac muscle contractility, *wherein an effect of said drug or drugs on said muscle interacts with an effect of said non-excitatory current.*

9. A method according to any one of claims 1, 2, and 8 *and 20–24*, wherein the change in cardiac muscle contractility is designed at least partially to compensate for cardiac muscle contractility decrease induced by said drug or mixture of drugs.

11. A method according to any one of claims 1, 2, [and] 8, *and 20–24*, wherein the change in cardiac muscle contractility is designed to add to and/or amplify the cardiac muscle contractility increase or decrease induced by said drug or mixture of drugs.

12. A method according to any one of claims 1, 2, [and] 8, *and 20–24*, for reducing the dosage of a cardiovascular drug which affects cardiac muscle contractility.

13. A method according to any one of claims 1, 2, [and] 8, *and 20–24*, for reducing the dosage of a cardiovascular drug which affects the electrophysiological characteristics of the cardiac muscle.

14. A method for the combined drug/electric-stimulation treatment of a cardiac muscle, comprising:

administering to a patient in need thereof a drug which affects the cardiovascular system and which affects the cardiac muscle, or a mixture of two or more such drugs;

providing an electric potential between at least a pair of electrodes in the vicinity of the cardiac muscle at at least two root locations;

causing a non-excitatory electric current to flow between said at least two contacting locations; and controlling the start time, duration and magnitude of the electric current flowing between said at least two root locations, so as to impart the desired change in cardiac muscle contractility, *wherein an effect of said drug or drugs on said muscle interacts with an effect of said non-excitatory current.*

15. A method according to [claim] *any of claims* 14 *or 25–29*, wherein the means for causing a non-excitatory electric current to flow, are synchronized to heart activity.

19. Apparatus [according to claim 20] *for the combined drug/electric-stimulation treatment of a cardiac muscle*, comprising:

means for creating an electric potential between at least a pair of electrodes in the vicinity of the cardiac muscle at at least two root locations;

means for causing a non-excitatory electric current to flow between said at least two root locations;

means for controlling the start time, duration and magnitude of the electric current flowing between said at least two root locations; and means for superimposing on the DC signal one or more waveforms of given frequency and amplitude, thereby to generate a complex signal.

*20. A method according to claim 1, wherein said controlling comprises controlling using an implantable controller.*

21. A method according to claim 1, wherein said treatment comprises treatment heart failure.

22. A method according to claim 1, wherein said desired change in a contractility comprises an increase in contractility.

23. A method according to claim 1, wherein said drug or mixture of drugs comprises a beta blocker.

24. A method according to claim 1, wherein said drug or mixture of drugs and said controlling act directly on same muscle tissue.

25. A method according to claim 14, wherein said controlling comprises controlling using an implantable controller.

26. A method according to claim 14, wherein said treatment comprises treatment heart failure.

27. A method according to claim 14, wherein said desired change in a contractility comprises an increase in contractility.

28. A method according to claim 14, wherein said drug or mixture of drugs comprises a beta blocker.

29. A method according to claim 14, wherein said drug or mixture of drugs and said controlling act directly on same muscle tissue.

30. A method for the combined drug/electric stimulation treatment of a cardiac muscle, comprising a) administering to a patient in need thereof a drug which affects the cardiovascular system and which affects the cardiac muscle, or a mixture of two or more such drugs, b) creating a non-excitatory electric potential between at least two points located in the vicinity of the muscle, and c) controlling one or more of the parameters consisting of start time, duration, magnitude and polarity of the non-excitatory electric potential created between said at least two points, wherein an effect of said drug or drugs on said muscle interacts with an effect of said non-excitatory potential on said muscle, and wherein said interaction comprises counteracting a pro-arrhythmic effect of said drug or drugs.

* * * * *